(12) United States Patent
Stanfield et al.

(10) Patent No.: US 10,833,451 B2
(45) Date of Patent: Nov. 10, 2020

(54) ELECTRICAL CONNECTOR

(71) Applicant: VADovations, Inc., Oklahoma City, OK (US)

(72) Inventors: J. Ryan Stanfield, Salt Lake City, UT (US); Timothy R. Maher, Hamilton, MO (US); Trevor A. Snyder, Edmond, OK (US); Andrew Matthews, Moore, OK (US)

(73) Assignee: VADovations, Inc., Oklahoma City, OK (US)

( * ) Notice: Subject to any disclaimer, the term of this patent is extended or adjusted under 35 U.S.C. 154(b) by 0 days.

(21) Appl. No.: 16/601,543

(22) Filed: Oct. 14, 2019

(65) Prior Publication Data

US 2020/0083638 A1 Mar. 12, 2020

Related U.S. Application Data

(63) Continuation of application No. 16/126,117, filed on Sep. 10, 2018, now Pat. No. 10,483,690.

(51) Int. Cl.
*H01R 13/62* (2006.01)
*H01R 13/627* (2006.01)
*H01R 13/703* (2006.01)
*H01R 13/20* (2006.01)
*H01R 13/635* (2006.01)
(Continued)

(52) U.S. Cl.
CPC ....... *H01R 13/6275* (2013.01); *A61N 1/3787* (2013.01); *H01R 13/08* (2013.01); *H01R 13/111* (2013.01); *H01R 13/20* (2013.01); *H01R 13/44* (2013.01); *H01R 13/635* (2013.01); *H01R 13/703* (2013.01); *A61N 1/362* (2013.01);
(Continued)

(58) Field of Classification Search
CPC .... H01R 13/6275; H01R 13/08; H01R 13/11; H01R 13/20
USPC .......................................... 439/352
See application file for complete search history.

(56) References Cited

U.S. PATENT DOCUMENTS 4,017,139 A * 4/1977 Nelson ................. F16L 37/133
439/352
4,947,115 A * 8/1990 Siemon ................. H01R 31/08
324/72.5

(Continued)

OTHER PUBLICATIONS

Bal Seal Engineering, Inc., "Products: Contacts for medical applications", printed from www.balseal.com/medical-contacts on Dec. 9, 2017.

(Continued)

*Primary Examiner* — Alexander Gilman
(74) *Attorney, Agent, or Firm* — Martin & Associates, LLC; Derek P. Martin

(57) ABSTRACT

An electrical connector includes a plug that mates with a receptacle. In a medical application, the plug is connected to electrical leads that pass through a patient's skin to an implanted medical device in the patient's body, while the receptacle is connected to external medical equipment. All electrical contacts in the plug are on internal portions. The receptacle includes annular contacts that contact the internal electrical contacts on the plug when the plug and receptacle are properly mated. The receptacle includes a plurality of annular electrical contacts that have a first diameter and are separated by a plurality of annular insulators having a second diameter smaller than the first diameter.

20 Claims, 17 Drawing Sheets

(51) Int. Cl.
*H01R 13/08* (2006.01)
*H01R 13/11* (2006.01)
*A61N 1/378* (2006.01)
*H01R 13/44* (2006.01)
*A61N 1/362* (2006.01)
*H01R 12/53* (2011.01)
*H01R 24/58* (2011.01)
*H01R 105/00* (2006.01)

(52) U.S. Cl.
CPC .............. *H01R 12/53* (2013.01); *H01R 24/58* (2013.01); *H01R 2105/00* (2013.01); *H01R 2201/12* (2013.01)

(56) References Cited

U.S. PATENT DOCUMENTS

| | | | | |
|---|---|---|---|---|
| 5,454,729 | A * | 10/1995 | Wen-Te | H01R 13/6273 439/357 |
| 5,871,371 | A * | 2/1999 | Rothenberger | H01R 9/038 439/579 |
| 6,129,577 | A * | 10/2000 | Daoud | H01R 13/20 439/482 |
| 6,302,725 | B1 * | 10/2001 | Daoud | H01R 31/08 439/482 |
| 6,511,339 | B1 * | 1/2003 | Huang | H01R 13/6275 439/275 |
| 6,692,287 | B2 * | 2/2004 | Yasuda | H01R 13/6275 439/352 |
| 7,384,300 | B1 | 6/2008 | Salgado et al. | |
| 7,563,123 | B2 * | 7/2009 | Cave | H01R 13/6395 439/369 |
| 7,844,329 | B2 | 11/2010 | Chambers | |
| 8,011,942 | B2 * | 9/2011 | Ohmori | H01R 13/6315 439/314 |
| 8,025,506 | B2 * | 9/2011 | Cairns | H01R 13/523 439/201 |
| 8,328,574 | B1 * | 12/2012 | Lin | H01R 13/6275 439/321 |
| 8,880,181 | B2 * | 11/2014 | Chambers | H01R 4/029 607/57 |
| 9,281,618 | B2 * | 3/2016 | Kurumizawa | B60L 3/04 |
| 9,306,342 | B2 | 4/2016 | Sellmer et al. | |
| 9,437,972 | B2 * | 9/2016 | Endo | H01R 13/6315 |
| 9,444,198 | B2 | 9/2016 | Sunaga et al. | |
| 9,793,618 | B2 * | 10/2017 | Sone | H01R 24/38 |
| 10,483,690 | B1 * | 11/2019 | Stanfield | H01R 13/111 |
| 10,673,179 | B1 * | 6/2020 | Harris | H01R 13/6683 |
| 2005/0009390 | A1 * | 1/2005 | Barker | H01R 13/631 439/188 |
| 2005/0173395 | A1 * | 8/2005 | Haussner | G01L 23/22 219/270 |
| 2008/0281158 | A1 * | 11/2008 | Miyagi | A61B 1/00124 600/152 |
| 2009/0215296 | A1 * | 8/2009 | Chambers | A61N 1/3752 439/271 |
| 2014/0036421 | A1 | 2/2014 | Lieba | |

OTHER PUBLICATIONS

Deringer-Ney, "Custom Connectors, Medical interconnect", printed from http://www.deringerney.com/products-and-capabilities/medical-materials/medical-interconnects on Dec. 9, 2017.
Fischer Connectors, "Ultimate" connector brochure, Dec. 13, 2017.
Oscor.com, "Lead Adaptors, IS4/DF4", printed from http://www.oscor.com/lead-adaptors-and-extensions/is4-df4-plug on Oct. 19, 2017.
Lemo, "T SERIES IP 68 Push-Pull Connectors", product brochure, Nov. 2017.

* cited by examiner

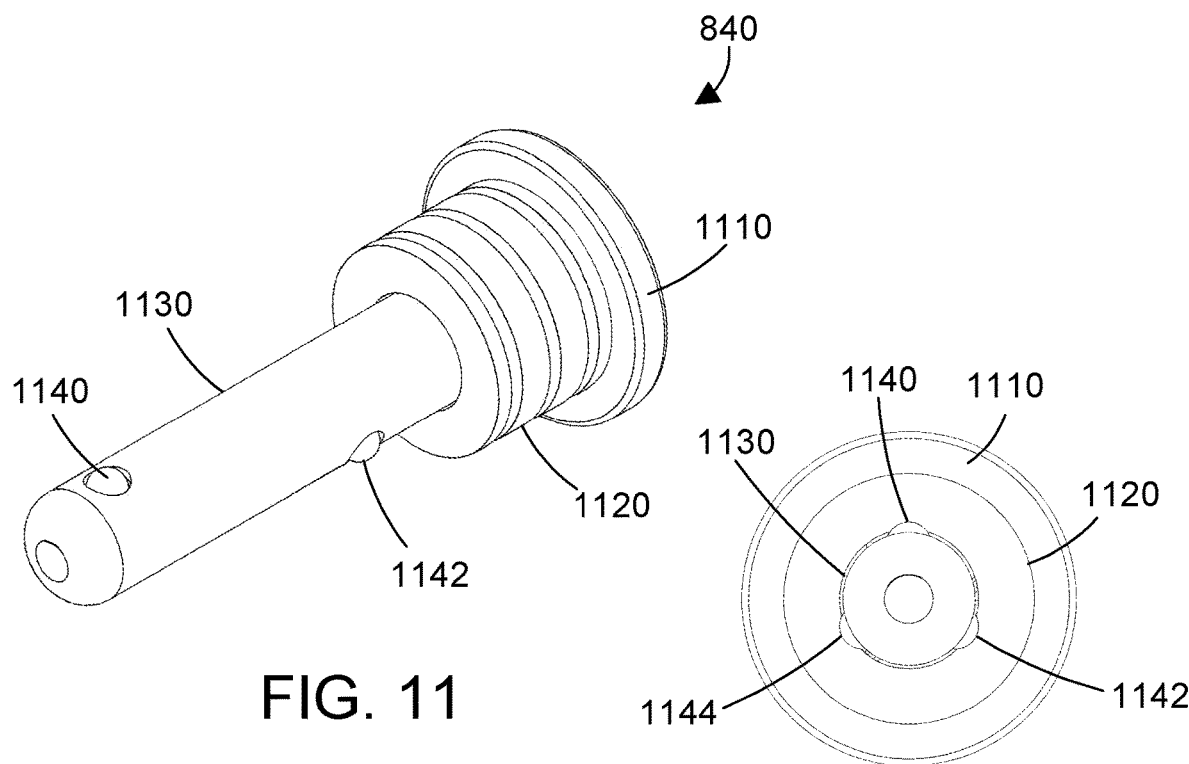
FIG. 11
FIG. 12
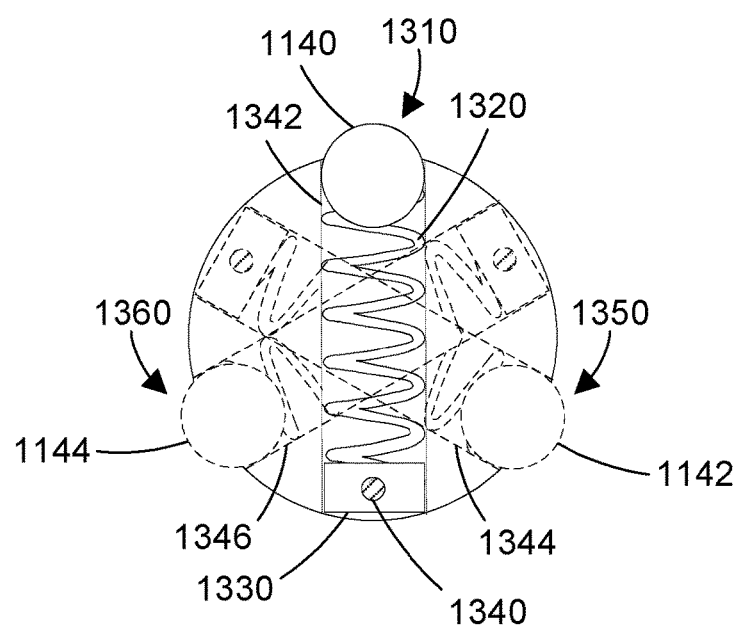
FIG. 13

ELECTRICAL CONNECTOR

BACKGROUND

1. Technical Field

This disclosure generally relates to electrical systems, and more specifically relates to an electrical connector.

2. Background Art

A myriad of different electrical connectors have been developed for numerous different applications. One specific application that requires specialized connectors is connectors for medical devices or equipment. For example, a pacemaker typically includes a connector that allows connecting the electrodes in the heart to the pacemaker. Because a pacemaker is implanted inside a patient's body, the connector must be sealed so no bodily fluids can enter the pacemaker. Other medical devices may be implanted in a patient's body, but require electrical leads that pass outside the body that are connected to external medical equipment. Examples of such devices include a total artificial heart (TAH), a ventricular assist device (VAD), and neurostimulators, including transcutaneous electrical nerve stimulators (TENS), percutaneous electrical nerve stimulators (PENS), transcranial magnetic stimulation (TMS), and percutaneous cochlear implant systems (PCIS).

Connectors for electrical leads that pass from a person's body to external equipment have different requirements than implantable connectors due to safety concerns. An electrical connector connected to a device in a person's body that is small enough to be put into an electrical outlet, for example, poses a shock hazard for the patient. Known connectors for connecting external equipment to an implanted device suffer from various disadvantages.

BRIEF SUMMARY

An electrical connector includes a plug that mates with a receptacle. In a medical application, the plug is connected to electrical leads that pass through a patient's skin to an implanted medical device in the patient's body, while the receptacle is connected to external medical equipment. All electrical contacts in the plug are on internal portions. The receptacle includes annular contacts that contact the internal electrical contacts on the plug when the plug and receptacle are properly mated. The receptacle includes a plurality of annular electrical contacts that have a first diameter and are separated by a plurality of annular insulators having a second diameter smaller than the first diameter.

The foregoing and other features and advantages will be apparent from the following more particular description, as illustrated in the accompanying drawings.

BRIEF DESCRIPTION OF THE SEVERAL VIEWS OF THE DRAWING(S)

The disclosure will be described in conjunction with the appended drawings, where like designations denote like elements, and:

FIG. 11 is a perspective view of the contact assembly in the receptacle shown in FIGS. 8-10;

FIG. 12 is an end view of the contact assembly in FIG. 11 in accordance with a first implementation;

FIG. 13 is an enlarged cross-sectional view of the contact assembly in FIGS. 11-12 showing the internal electrical contacts;

DETAILED DESCRIPTION

Figure 1:
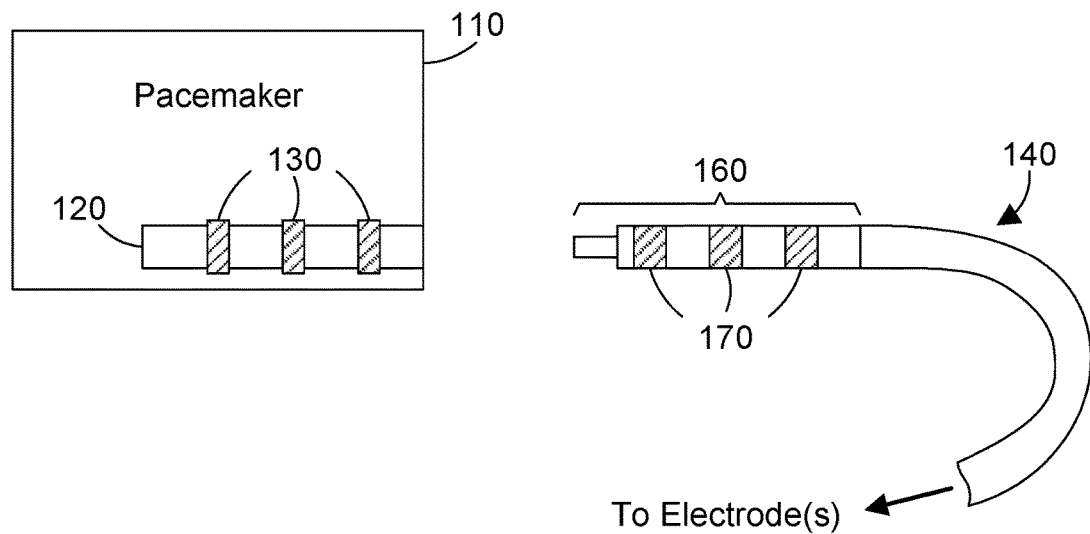
FIG. 1 illustrates a known connector used in a prior art pacemaker.

Implantable medical devices give rise to the need for specialized electrical connectors. Referring to FIG. 1, a prior art pacemaker 110 is shown with a receptacle 120 that includes three electrical contacts 130, which are electrically connected to the pacemaker circuitry, which is not shown in FIG. 1. Electrodes that are designed for use with the pacemaker include a cable 140 that includes a plug 160 that includes three electrical contacts 170. When the plug 160 is inserted and properly mated to the receptacle 120, the three electrical contacts 170 on the plug make electrical contact with the three electrical contacts 130 in the receptacle 120, thereby connecting the electrodes to the circuitry in the pacemaker. Bal Conn connectors are suitable for use in pacemakers, such as the connector illustrated in FIG. 1. Bal Conn is a registered trademark of Bal Seal Engineering, Inc.

A plug that includes external contacts such as plug 160 in FIG. 1 is not suitable for connecting an implanted device to external equipment. International Electric Code 60601-1 specifies standards for medical equipment. Subclause 8.5.2.3 addresses patient leads or patient cables, and specifies there should be no possibility of connecting the patient accidentally to things that could deliver an electrical shock to the patient. Thus, a connector that has external contacts as shown in FIG. 1 could be placed in an electrical outlet, which would cause power to flow from the outlet through the exposed contacts 170 to the patient. The connector shown in FIG. 1 would therefore likely violate IEC 60601-1 Subclause 8.5.2.3 if it were used to connect an implanted device to external electrical equipment.

Connectors that are used to attach implanted devices to external equipment thus have different requirements than connectors that do not have a connection outside the body. Examples of one known prior art connector that might be used to connect an implanted device to external equipment is shown at 210 in FIG. 2. Specific examples of known connectors similar to the prior art connector 210 shown in FIG. 2 include the T-series IP 68 Push-Pull Connectors from Lemo USA, Inc., and the UltiMate connectors from Fischer Connectors SA. The prior art connector 210 shown in FIG. 2 includes a plug portion 220 connected to a cable 240 that mates to a receptacle portion 230 connected to a cable 250. We assume for this example cable 240 is connected to an implanted device, and cable 250 is connected to external equipment. Connector 210 does not have exposed contacts like the pacemaker plug 160 shown in FIG. 1, thereby reducing the shock hazard to a patient. Note, however, the diameter D1 of the plug 220 is substantially larger than the diameter D2 of the cable 240 that attaches to the plug 220. This means an incision must be made in the patient's skin that is large enough to accommodate the diameter D1 of the plug 220 so the plug 220 can be passed from the implanted device inside the patient's body through the skin to the connector 230 that is connected to the external equipment. Having an incision that is large enough to accommodate the larger diameter D1 of the plug 220 results in an incision that is larger than is needed for cable 240, which can provide a site for infection. In addition, the plug 220 and receptacle 230 typically include pins that require a specific orientation between plug 220 and receptacle 230 in order for the two to be connected.

Figure 2:
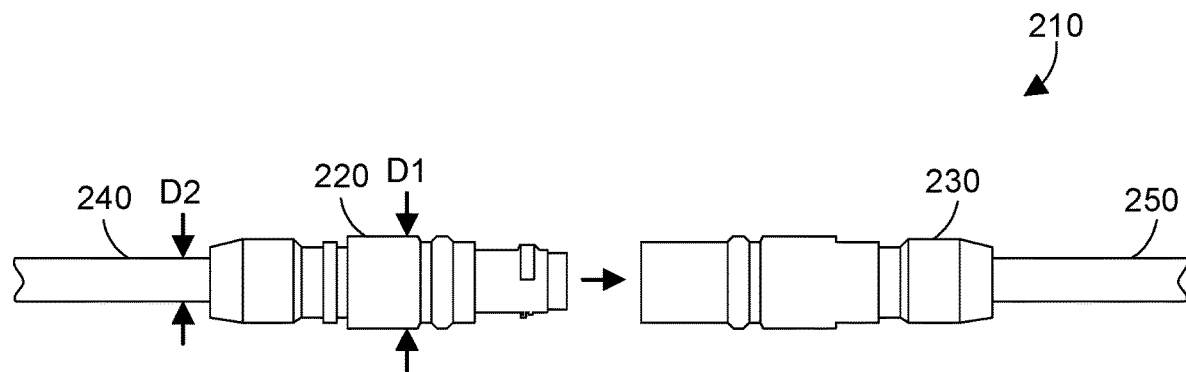
FIG. 2 illustrates a known connector used for connecting an implanted device to external medical equipment.

To summarize, implanted connectors that have external contacts as shown in FIG. 1 are not suitable for use outside the body due to risk of shock. Known connectors such as shown in FIG. 2 can be used to connect an implanted device to external equipment, but these connectors require an incision that is significantly larger than the cable, creating a risk of infection at the site where the cable passes through the skin, and these connectors require a specific orientation to be mated together. The connector disclosed herein solves these problems.

An electrical connector includes a plug that mates with a receptacle. In a medical application, the plug is connected to electrical leads that pass through a patient's skin to an implanted medical device in the patient's body, while the receptacle is connected to external medical equipment. All electrical contacts in the plug are on internal portions. The receptacle includes annular contacts that contact the internal electrical contacts on the plug when the plug and receptacle are properly mated. The receptacle includes a plurality of annular electrical contacts that have a first diameter and are separated by a plurality of annular insulators having a second diameter smaller than the first diameter.

Figure 3:
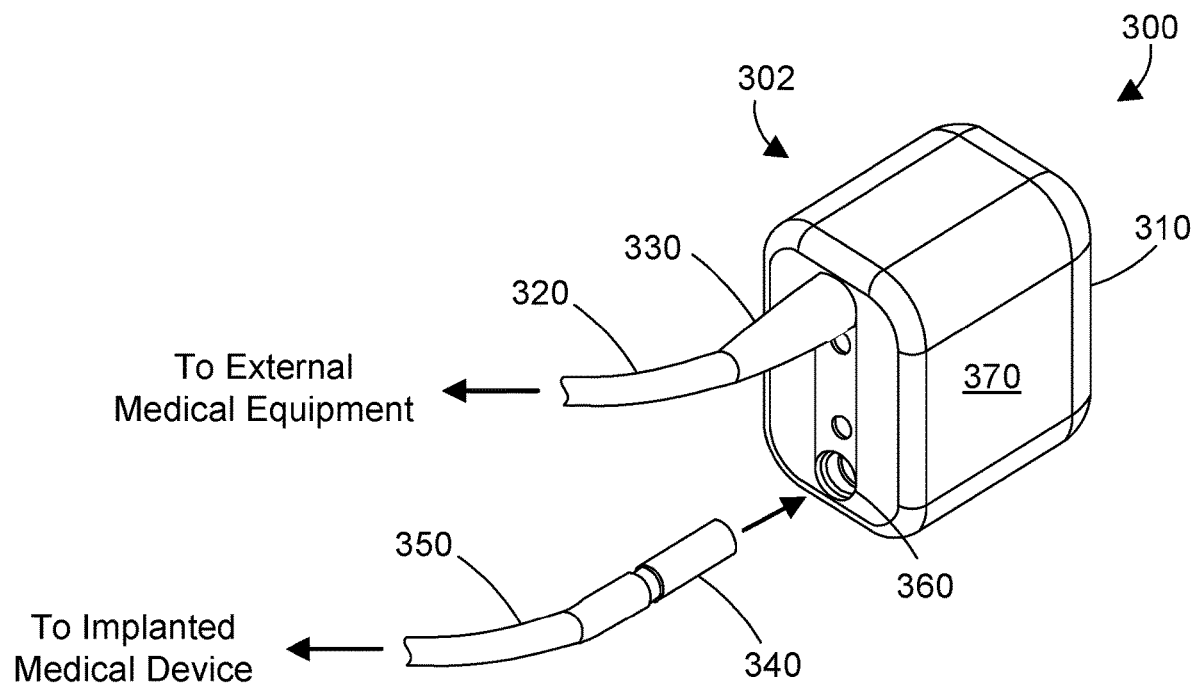
FIG. 3 illustrates one suitable implementation for an electrical connector within the scope of the claims and disclosure herein.

Referring to FIG. 3, a connector 300 includes a plug 340 that mates to a receptacle 302. The plug 340 is connected to a cable 350, which is connected to an implanted medical device. A cable 320 that is connected on one end to external medical equipment is connected at the other end through a strain relief 330 to the receptacle 302. The receptacle 302 includes a housing 310, two opposed movable release buttons 370 for releasing the plug, and an opening 360 for receiving the plug 340. Note that only one of the movable release buttons 370 is shown in FIG. 3.

Figure 4:
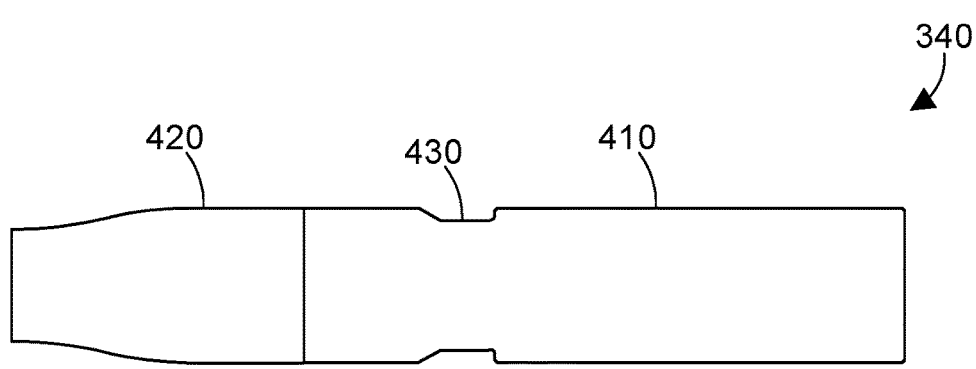
FIG. 4 is a side view of the plug shown in FIG. 3.
Figure 5:
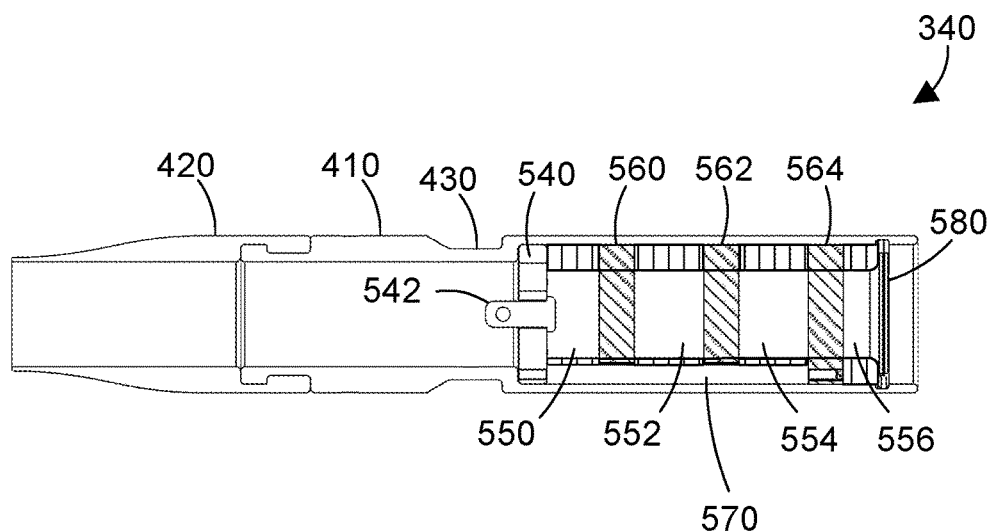
FIG. 5 is a cross-sectional view of the plug shown in FIGS. 3 and 4 showing its internal structure.

FIG. 4 shows an enlarged side view of the plug 340 shown in FIG. 3. Plug 340 includes a substantially rigid body portion 410 coupled to a flexible strain relief 420. The body portion 410 includes an annular recess 430 that allows locking the plug 340 into place in the receptacle 302. A cross-sectional view of the plug 340 in FIGS. 3 and 4 is shown in FIG. 5 to illustrate its internal structure. The body portion 410 includes a printed circuit board 540 that provides electrical connections between wires in the cable, which is not shown in FIG. 5, and the electrical contacts 560, 562 and 564. The printed circuit board could be any suitable type of printed circuit board, whether currently known or developed in the future. A common type of known printed circuit board is a fiberglass-epoxy printed circuit board. The printed circuit board 540 also includes a post 542 for connecting a structural member of the cable, such as a reinforcing wire, to the printed circuit board. The electrical contacts 560, 562 and 564 are separated by insulators 550, 552 and 554, and have an additional insulator 556 at the end. Each electrical contact 560, 562 and 564 is electrically connected to a different contact point on the printed circuit board 540. By way of example, a wire 570 is shown in FIG. 5 that connects printed circuit board 540 to the electrical contact 564. The wire 570 preferably includes insulation that is stripped from the ends so the ends can be electrically connected to the printed circuit board 540 and the electrical contact 564. In one particular implementation, the stripped ends of wire 570 are soldered to the printed circuit board 540 and to the electrical contact 564. Of course, any suitable electrical connection could be used within the scope of the disclosure and claims herein. For example, if the wires are drawn-filled tubes (DFTs), they cannot be soldered, but could be laser welded or mechanically crimped to the printed circuit board and to the respective electrical contact. It is understood that electrical contacts 560 and 562 have corresponding wires that electrically connect these contacts to the printed circuit board 540, even though these are not shown in FIG. 5.

Figure 6:
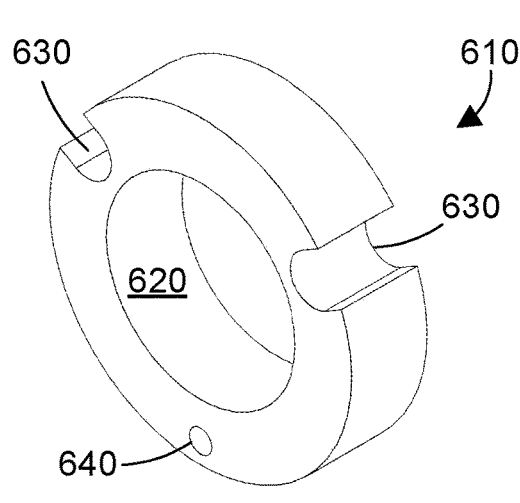
FIG. 6 is a perspective view of one specific implementation of a conductor ring shown in FIG. 5.
Figure 7:
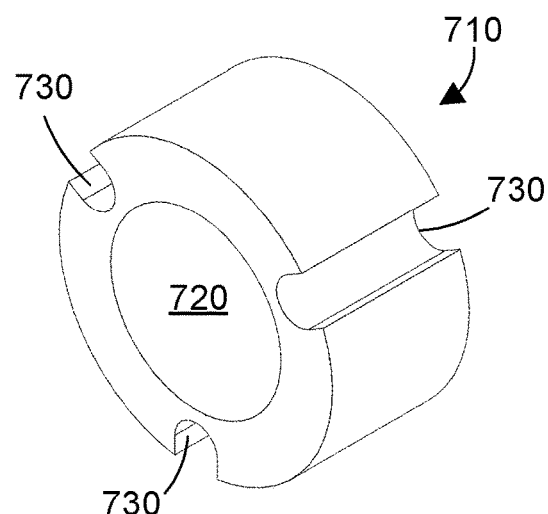
FIG. 7 is a perspective view of one specific implementation of an insulator ring shown in FIG. 5.

While the electrical contacts 560, 562 and 564 and the insulators 550, 552, 554 and 556 appear in the cross-sectional view in FIG. 5 to be rectangular strips, these are actually annular rings as shown in FIGS. 6 and 7. Electrical contact 610 in FIG. 6 is one suitable implementation for the electrical contacts 560, 562 and 564 shown in FIG. 5. Electrical contact 610 includes a hollow circular interior portion 620, two outside recesses 630, and a connection point 640. The two outside recesses 630 and connection point 640 are most preferably at 120 degree angles from each other, so the three are equally-spaced along the circumferences of the electrical contact 610. Of course, these could be spaced at different angles as well. The connection point 640 is the point where the wire is connected (e.g., soldered), such as shown at the bottom of electrical contact 564 in FIG. 5. The outside recesses 630 allow wires for the other electrical contacts to pass. Each electrical contact 560, 562 and 564 is rotated 120 degrees with respect to its neighbor so the contact point 640 of each aligns with the outside recesses 630 of the neighbor(s).

The insulator 710 in FIG. 7 is one suitable implementation for the insulators 552 and 554 shown in FIG. 5. The insulator 710 includes a hollow circular interior portion 720 and three outside recesses 730. The outside recesses 730 provide a place for the wires to run that connect the printed circuit board 540 to the electrical contacts 560, 562 and 564. While insulators 550 and 556 have slightly different dimensions and/or configurations than insulators 552 and 554, they preferably include outside recesses similar to the outside recesses 730 shown in FIG. 7.

With the configuration shown in FIGS. 5-7, the inside portion of plug 340 can be manufactured as follows. Note the steps it the manufacturing process are provided by way of example, and any suitable steps or sequence could be used. The printed circuit board 540 is placed in a desired position. Three wires are soldered into the printed circuit board 540 into three holes that are most preferably 120 degrees apart near the perimeter of the printed circuit board. The insulator 550 is placed next to the printed circuit board so the three wires pass through the three outside recesses (see 730 in FIG. 7). The electrical contact 560 is placed next to insulator 550, then connected to the correct one of the three wires at its contact point (see 640 in FIG. 6). The remaining two wires are placed in the outside recesses 630 of contact point 560. The next insulator 552 is then placed next to the electrical contact 560 so the two remaining wires pass through two of the outside recesses. The electrical contact 562 is placed next to insulator 552, then connected to the correct one of the two remaining wires at its contact point. The next insulator 554 is then placed next to the electrical contact 562 so the remaining one wire passes through one of the outside recesses. The electrical contact 564 is placed next to the insulator 554, then soldered to the one remaining wire at its contact point. The next insulator 556 is then placed next to the electrical contact 564. Note these pieces could be secured together using any suitable means. For example, adhesive could be used to connect each piece to the next. In the alternative, structural attachments could be used, such as three small posts at 120 degree angles on each piece that fit into corresponding three small recesses on each piece when the two are properly aligned. The result is a stack that includes the printed circuit board 540, insulator 550, electrical contact 560, insulator 552, electrical contact 562, insulator 554, electrical contact 564, and insulator 556. A cable can then be run through the strain relief 420 and through the body portion 410 so the wires of the cable are exposed out the right end of the plug shown in FIGS. 4 and 5. At this point the structural wire in the cable can be soldered to the post 542 on the printed circuit board 540, and three electrical wires in the cable can be mechanically attached to the correct locations on the printed circuit board 540. At this point all needed contacts between the cable and the printed circuit board have been made. The cable can then be pulled so the stack that includes the printed circuit board, insulators and electrical contacts is pulled within the body portion 410 until properly seated in place. At this point, one or more retaining members could be used to hold the stack in place. As an example, FIG. 5 shows an annular retaining ring 580 that is snapped into place to hold the internal stack in place. Of course, any suitable retaining member could be used. For example, one or more plastic tabs could be provided so that once the stack is slid into place, the plastic tabs captivate the stack so it cannot move. In another example, one or more set screws could be used. The disclosure and claims herein extend to any suitable retaining member or mechanism. Note the sequence described above for assembling the plug can vary. For example, the cable could be inserted through the strain relief 420 and body portion 410, and can be soldered or otherwise electrically connected to the printed circuit board 540 before the stack is created. The disclosure and claims herein expressly extend to any suitable sequence for assembling the plug 340.

Figure 8:
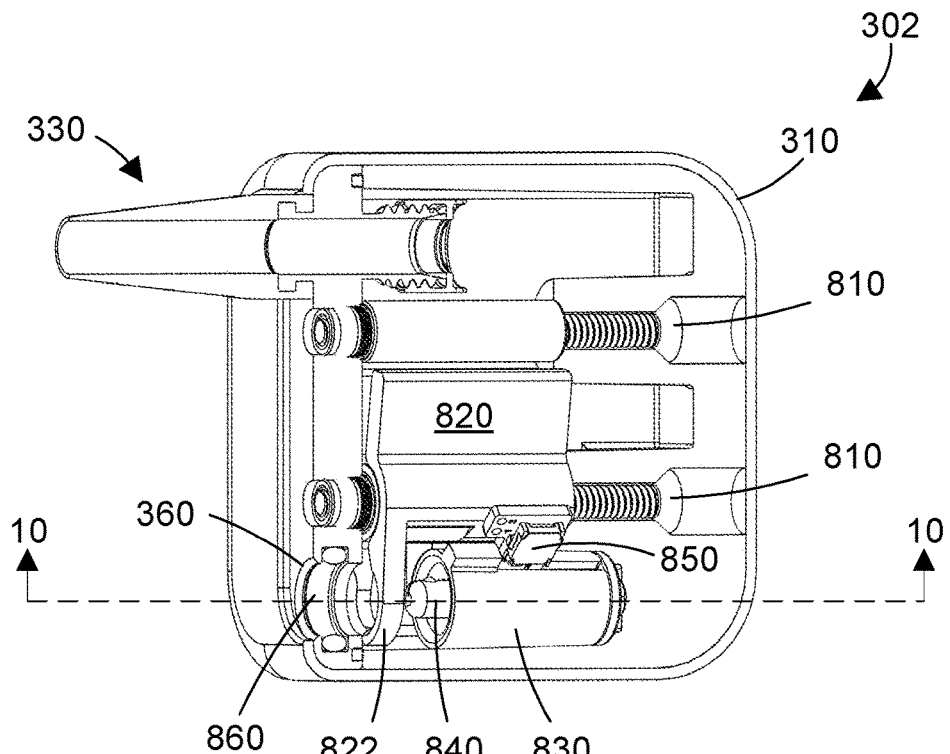
FIG. 8 is a partial side cutaway view of the receptacle shown in FIG. 3.

One suitable implementation for the receptacle 302 is shown in FIG. 8, which is a partial cutaway view showing some of the internal features of the receptacle 302. The housing 310 provides a strain relief 330 through which a cable that is to be connected to some external equipment is run. The cable is not shown in FIG. 8. The cable will have multiple wires that are connected to the contact assembly 840, such as by soldering the wires to connections on a printed circuit board that is part of the contact assembly 840. Two screws 810 are used to connect different pieces in the receptacle 302 together. A retention arm 820 is shown with its corresponding tip portion 822 that engages the annular recess 430 on the plug 340 when the plug 340 is properly mated to the receptacle 302. An outer housing 830 has a substantially cylindrical shape, and surrounds most of the contact assembly 840. A switch 850 is provided as one suitable form for a connection detection sensor. When the plug is within the receptacle, the switch is in one state, and when the plug is not within the receptacle, the switch is in an opposite state. For example, the switch could be normally open when the plug is not within the receptacle, and when the plug is inserted into the receptacle, the plug actuates the switch 850, thereby closing the switch and providing an indication that the plug is within the receptacle. The opening 360 of receptacle 302 is shown to include an O-ring 860 that seals around the body portion 410 of the plug 340 when the plug 340 is inserted into the opening 360 of receptacle 302, to seal the junction between the plug 340 and the receptacle 302 to be fluid-tight.

Figure 9:
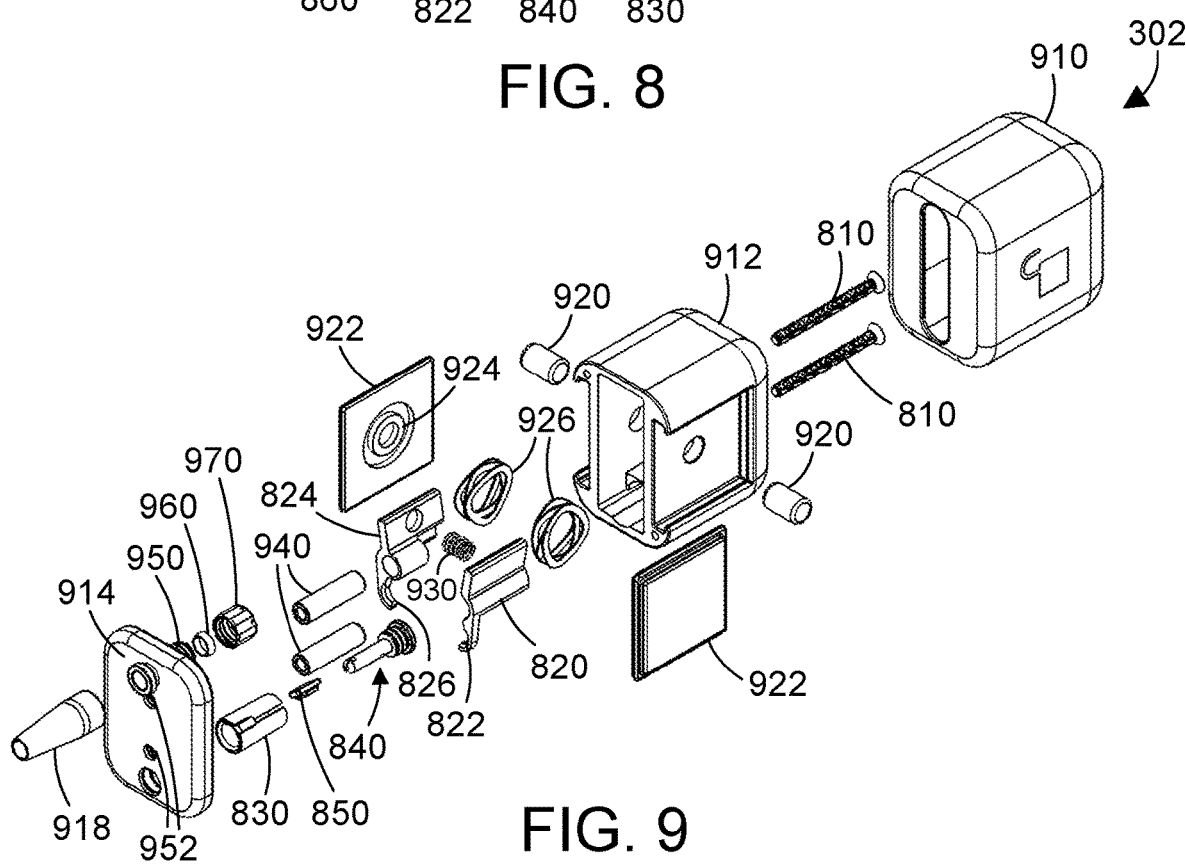
FIG. 9 is an exploded view of the receptacle in FIGS. 3 and 8 showing its internal components.

FIG. 9 shows an exploded view of the receptacle 302 shown in FIG. 8. Strain relief 330 in FIG. 8 includes a rubber portion 918 coupled to a rigid portion 950 that is coupled via a washer 960 and nut 970 to the front face 914 of the receptacle 302. The outer housing 830 and switch 850 described above with respect to FIG. 8 are shown in FIG. 9. Two bushings 940 are spacers through which the screws 810 pass to connect the main housing 912 to the front face 914. Front face 914 preferably includes two threaded holes 952 that receive the screws 810 to secure the front face 914 to the main housing 912. The bottom bushing 940 passes through the two retention arms 820 and 824, providing a common pivot point for the two retention arms 820 and 824. A spring 930 is installed in recesses in the upper portions of the two retention arms 820 and 824, and presses the two retention arms 820 and 824 apart, which causes the corresponding tip portions 822 and 826 to be biased in a closed position due to the scissor-like action of the two retention arms 820 and 824. Due to spring 930, the retention arms 820 and 824, and their corresponding tip portions 822 and 826, are spring-loaded. Tip portions 822 and 826 preferably include a substantially semicircular configuration so the two tip portions can lock into the annular recess in the plug. Two opposed movable release buttons 922 are installed into the main housing 912, with pegs 920 that contact the top portions of the retention arms 820 and 824. Release buttons 922 have two corresponding springs 926 that bias the release buttons 922 outward, so the release buttons 922 are biased in a non-depressed state, as shown at 370 in FIG. 3. A peg 920 and spring 926 preferably are installed in corresponding recesses 924 in each release button 922. A user can press the two opposed release buttons 922 simultaneously by pressing one with a thumb and the other with a finger, for example, which will cause the tops of the retention arms 820 and 824 to be pushed towards each other, which will cause the tip portions 822 and 826 to separate from each other, thereby disengaging the tip portions 822 and 826 from the annular recess in the plug. A person thus releases a plug that is locked into place in the receptacle by the tip portions 822 and 826 of the retention arms 820 and 824 by pressing simultaneously on the release buttons 922, which disengages the tip portions 822 and 826 from the annular recess on the plug. A flexible polymer covering 910 is provided to encase and thereby protect the assembled receptacle 302.

Figure 10:
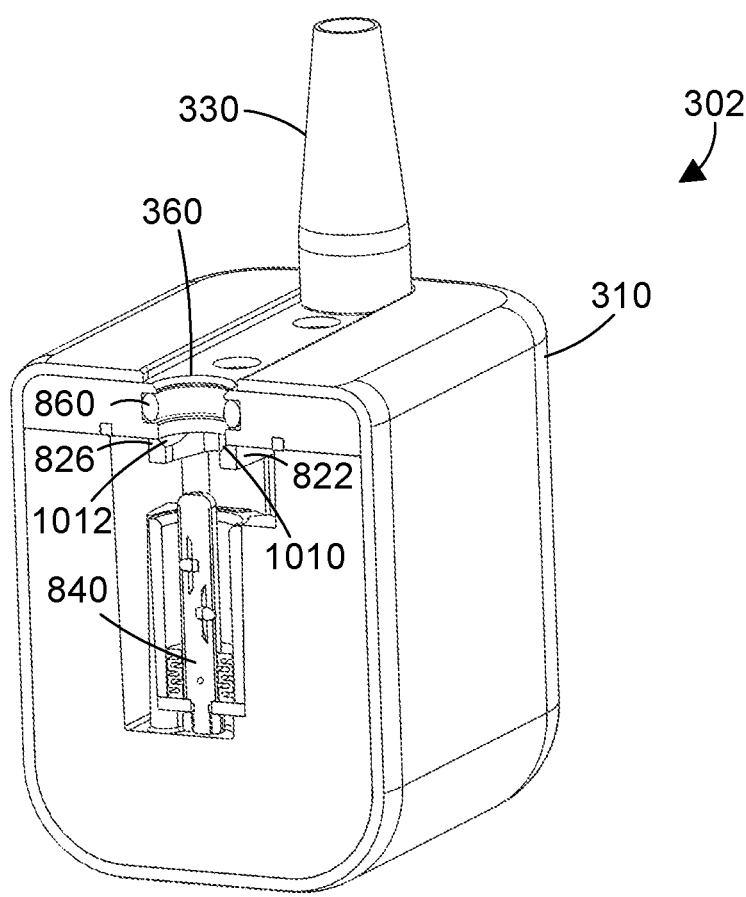
FIG. 10 is a bottom cross-sectional view of the receptacle shown in FIG. 8 taken along the line 10-10.

FIG. 10 is a partial cross-sectional view of the receptacle 302 in FIG. 8 taken along the line 10-10. The contact assembly 840 is shown, along with the strain relief 330, and the opening 360 that includes the O-ring 860. FIG. 10 shows in more detail that the tip portions 822 and 826 of the retention arms each have a beveled front. Thus, tip portion 822 includes a beveled front 1010, and tip portion 826 includes a beveled front 1012. With this arrangement, when the plug contacts the beveled fronts 1010 and 1012, the plug will slide along the beveled fronts 1010 and 1012, thereby separating the tip portions 822 and 826 a sufficient distance for the plug to pass between the tip portions 822 and 826. Because the retention arms have a spring that provides a bias force to keep the tip portions 822 and 826 together, the plug sliding along the beveled fronts 1010 and 1012 forces the tip portions 822 and 826 apart against the bias of the spring. When the plug is fully seated in the receptacle 302, the tip portions 822 and 826 will engage the annular recess 430 shown in FIG. 4, thereby locking the plug 340 in place. Note, however, that even though the plug is locked in position with respect to the receptacle, the plug can still be rotated in any direction while maintaining the electrical connections between the plug and the receptacle. In addition, no special keying or orientation is needed to mate the plug to the receptacle. The connection between the two is omnidirectional, meaning the plug can be in any suitable rotational relationship with respect to the receptacle.

One specific implementation for the contact assembly 840 is shown in FIGS. 11-14. The contact assembly 840 preferably includes a printed circuit board 1110, an ejection spring 1120, and a cylindrical body 1130 that includes multiple spring-loaded electrical contacts 1140, 1142 and 1144. FIG. 12 is an end view of the contact assembly 840 shown in FIG. 11. FIG. 13 is an enlarged cross-sectional view of the cylindrical body 1130 showing a spring assembly 1310 that has a ball head 1140 electrically coupled to a spring 1320, which is electrically coupled to a base 1330. The base 1330 of the spring assembly 1310 is electrically coupled to a wire 1340, which is electrically coupled to the printed circuit board 1110, which is connected to a cable that runs through the strain relief 330 into the receptacle 302. In this manner the electrical conductors in the cable are made available via the spring-loaded ball contacts of the spring assemblies shown in FIG. 13. Each spring assembly is placed in a corresponding cylindrical hole. Thus, spring assembly 1310 in FIG. 13 is placed within a corresponding cylindrical hole 1342. The other two spring assemblies 1350 and 1360 are placed within their corresponding holes 1344 and 1346, respectively, that are at a 120 degree angle with respect to hole 1350, thereby providing evenly-spaced electrical contacts around the circumference of the cylindrical body 1130. These other two spring assemblies 1350 and 1360 are shown in phantom in FIG. 13 for clarity. The specific example shown in the figures assumes three electrical contacts, which means each is at a 120 degree angle with respect to the other two. Note, however, the principles herein apply to any suitable number of electrical contacts, and any suitable spacing or arrangement. For example, if six electrical contacts are needed, there could be six different electrical contacts provided by six corresponding spring assemblies spaced in 60 degree increments. If four electrical contact are needed, there could be four different electrical contacts provided by four corresponding spring assemblies spaced in 90 degree increments. In addition, the spacing between electrical contacts need not be uniform. Thus, if four electrical contacts are needed, one spring assembly could be at zero degrees, a second at 45 degrees, a third at 90 degrees, and fourth at 225 degrees. This simple examples show the disclosure and claims herein expressly extend to any suitable number of electrical contacts at any suitable spacing or arrangement between electrical contacts.

Figure 14:
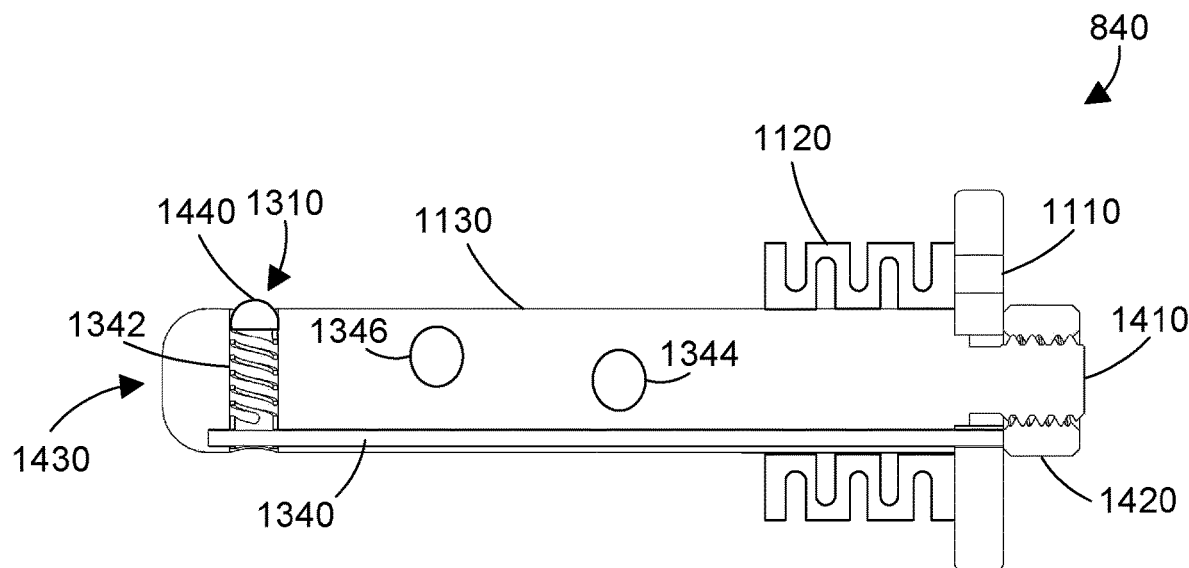
FIG. 14 is a side cross-sectional view of the first implementation of the contact assembly shown in FIGS. 11-13.

FIG. 14 is a cross-sectional view of the contact assembly 840 shown in FIGS. 11-13. The ejection spring 1120 is shown as a flexible material having baffles that give, allowing the plug to partially compress the ejection spring 1120 to be seated correctly in the receptacle 302. Note, however, the ejection spring 1120 could have other configurations as well. For example, the ejection spring 1120 could be a somewhat solid member, such as rubber or foam, that has the required resiliency to allow locking the plug into place in the receptacle. Of course, ejection spring 1120 could also be a metal spring. The ejection spring 1120 could be any suitable material and/or configuration that provides some linear resistance along the longitudinal axis of the cylindrical body 1130 such that when a plug first contacts the ejection spring 1120, the plug is not fully seated inside the receptacle, but by pressing the plug into the receptacle with some additional force, the ejection spring is partially compressed until the tip portions of the retention arms lock into place in the annular recess of the plug, thereby retaining the plug in a mated position with respect to the receptacle. In one suitable implementation, the retaining spring is preferably compressed less than 0.050 inch (1.3 mm) when the tip portions of the retention arms lock into place in the annular recess of the plug.

The ejection spring thus serves two functions. First, the ejection spring serves to assure the plug is properly mated to the receptacle by requiring compression of the ejection spring in order for the receptacle to lock the plug into place. Second, the ejection spring serves in the disconnection of the plug from the receptacle. When the two release buttons are pressed simultaneously, the ejection spring moves the plug to a position where the tip portions of the retention arms do not engage the annular recess in the plug when the two release buttons are no longer pressed. Thus, a person disconnecting the plug can depress the two release buttons, which will cause the plug to disengage from the retention arms and to move out of position from being locked by the retention arms. The plug can then be pulled out of the receptacle without a need for pressing the two release buttons while the plug is pulled out. In one preferred implementation, the plug can include a printed annular ring on the exterior that could provide a visual indication that the plug is correctly mated to the receptacle. In one implementation, the printed annular ring is located so that when the plug is properly mated with the receptacle, the printed annular ring is not visible. In another implementation, the printed annular ring is located so that when the plug is properly mated with the receptacle, the printed annular ring is next to the housing on the receptacle. Of course, many variations exist for visually indicating when the plug is or is not properly mated with the receptacle, all of which are within the scope of the disclosure and claims herein.

Spring assembly 1310 in FIG. 14 is shown with a semispherical head 1440 instead of a spherical ball-shaped head 1140 shown in FIGS. 11-13. This is shown to illustrate the heads of the electrical contacts can have any suitable shape and/or configuration. In the most preferred implementation, the heads of the electrical contacts are somewhat rounded to allow the heads to slide easily on the corresponding annular electrical contacts in the plug when the plug is rotated. The spring assemblies in the contact assembly provide a plurality of electrical contacts that contact the plurality of annular electrical contacts in the plug when the plug is mated to the receptacle.

FIG. 14 shows a wire 1340 that is used to connect the spring assembly 1310 to the printed circuit board 1110. In the most preferred implementation, the wire 1340 is soldered to the spring assembly 1310 and the printed circuit board 1110. Of course, the wire 1340 could be laser-welded, crimped, or attached using some other means to the spring assembly 1310 and/or the printed circuit board 1110. In one suitable implementation, the cylindrical body 1130 is made of a rigid plastic material that is extruded through a die that provides three longitudinal cylindrical channels in which the wires can be placed. The holes for the spring assemblies, such as holes 1342, 1344 and 1346 are drilled at 120 degree angles with respect to each other at a location where each hole intersects one of the three longitudinal cylindrical channels in which wires can be placed. The spring assemblies are then dropped into their respective holes and attached to the corresponding wire at the bottom of the hole. Note the cylindrical body 1130 in FIG. 14 includes the other two holes 1346 and 1344 drilled at 120 degree angles with respect to hole 1342, but the spring assemblies in these holes are not shown in FIG. 14 for the sake of clarity. The body portion 1130 preferably includes a rounded front 1430 as shown in FIG. 14 that eases the alignment of the plug onto the contact assembly 840.

The end of the cylindrical body 1130 that attaches to the printed circuit board 1110 may have a threaded portion 1410 that can receive a nut 1420 to attach the cylindrical body 1130 to the printed circuit board 1110. The printed circuit board 1110 preferably includes features that allow attaching conductors from a cable that runs through the strain relief into the receptacle to the printed circuit board, such as a connector, solder pads, etc.

Figure 15:
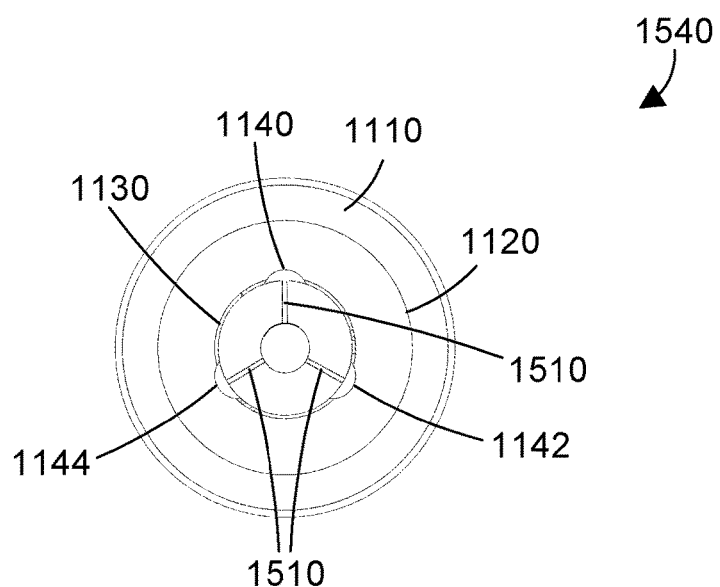
FIG. 15 is an end view of the contact assembly in FIG. 11 in accordance with a second implementation.
Figure 16:
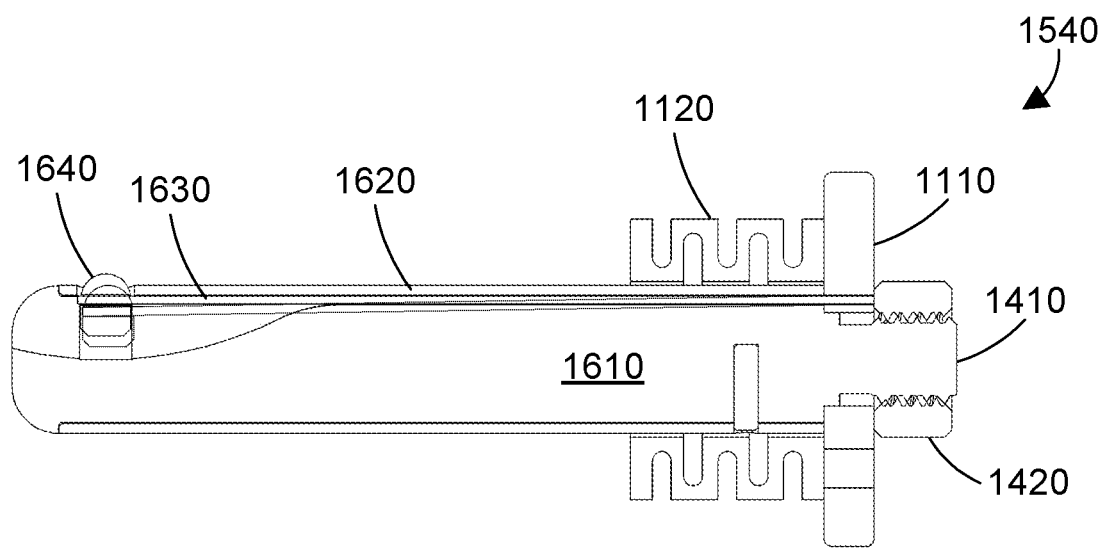
FIG. 16 is a side cross-sectional view of the second implementation of the contact assembly shown in FIG. 15.

A second specific implementation for the contact assembly 840 is shown as contact assembly 1540 in FIGS. 15 and 16. Contact assembly 1540 preferably includes three longitudinal slits 1510 for receiving spring wires that connect the spring-loaded electrical contacts 1140, 1142 and 1144 to the printed circuit board 1110. One of these spring wires is shown as spring wire 1630 in the cross-sectional view in FIG. 16. Spring wire 1630 is not just an electrical connection, but is stiff enough to provide a spring action for the spring-loaded electrical contact 1640, which is one suitable implementation for the spring-loaded electrical contact 1140 in FIGS. 11, 12 and 15. The spring-loaded electrical contact 1640 is connected to the spring wire 1630, which is connected to the printed circuit board 1110. The stiffness of the spring wire 1630 holds the spring-loaded electrical contact 1640 in the position shown in FIG. 16. When the spring-loaded electrical contact 1640 is pressed down slightly as the plug is inserted onto the contact assembly 1540, the spring bias provided by the spring wire is overcome so the spring-loaded electrical contact 1640 can retract slightly, as shown in phantom in FIG. 16. Because of the slits 1510, the contact assembly 1540 includes an outer sheath 1620 that covers the spring wires. In the most preferred implementation, the sheath 1620 has three holes that align with the three spring-loaded contacts, including spring-loaded contact 1640 shown in FIG. 16. The three spring wires are thus connected to the three spring-loaded electrical contacts, the spring wires are placed in their respective grooves while the spring-loaded electrical contacts are placed in their respective holes. At this point the sheath 1620 may be slipped over the center portion 1610 to captivate the spring wires and spring-loaded electrical contacts in place. At this point the spring wires may be attached to the printed circuit board 1110, which captivates the sheath 1620 in place.

Figure 17:
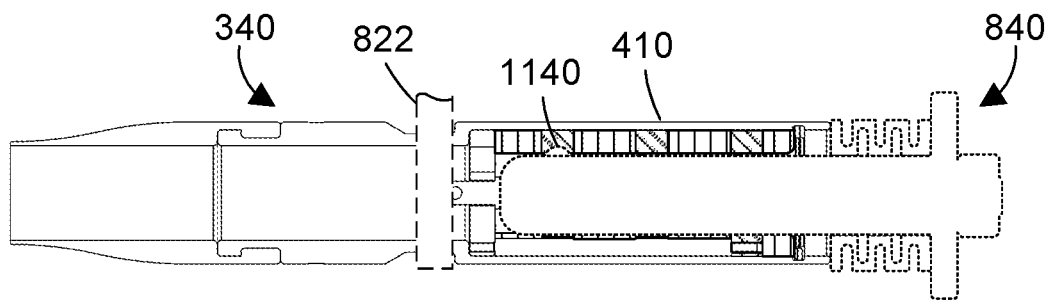
FIG. 17 is a side cross-sectional view showing the plug 340 mated to the contact assembly 840 of the receptacle to illustrate the electrical contacts.

FIG. 17 shows a plug 340 properly mated to the contact assembly 840 inside the receptacle 302. The contact assembly 840 is shown in phantom in FIG. 15 to make the difference clear between the plug 240 in solid lines and the contact assembly 840 in phantom. The plug 340 is initially pushed through the opening in the receptacle, which causes the leading edge of the plug to push on the beveled edges of the tip portions of the retention arms (see FIG. 10), which spreads the tip portions of the retention arms apart so the cylindrical body 410 can be pushed farther into the receptacle to engage the contact assembly 840. Once the leading edge of the plug contacts the ejection spring, additional force is applied to partially compress the ejection spring until the tip portions of the retention arms lock into the annular recess in the body portion of the plug. FIG. 17 shows the tip portion 822 of retention arm 820 shown in FIGS. 8-10 locking into the annular recess of the plug 340 to maintain the plug 340 in a mating position with respect to the contact assembly 840. Once the plug 340 is properly seated and locked into place via the retention arms, each contact point in the contact assembly 840 is in electrical contact with a corresponding annular conductor in the plug 340, as shown in FIG. 15.

Because the electrical contacts in the plug are annular in shape, the plug can be rotated freely while fully seated and engaged with the receptacle 302 while maintaining good electrical connections.

Figure 18:
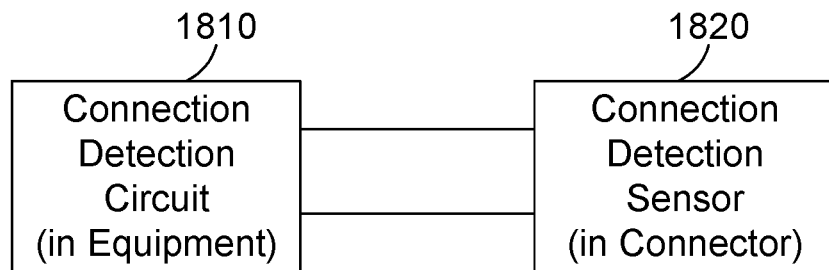
FIG. 18 is a block diagram of a circuit for detecting when the plug is mated to the receptacle.

FIG. 18 is a block diagram illustrating how a connection detection sensor 1820 in the receptacle 302 can provide an electrical signal to a connection detection circuit 1810 in external equipment to indicate when the plug 340 is within the receptacle 302. In one suitable configuration shown in FIGS. 8 and 9, the connection detection sensor 1820 is a switch 850 that is in one state (e.g., open) when the plug 340 is not within the receptacle 302, and is in a different state (e.g., closed), when the plug 340 is within the receptacle 302. Note, however, the connection detection sensor 1820 could be any suitable way of sensing when the plug 340 is or is not within the receptacle 302, including a magnetic reed switch that is actuated by a small magnet in the plug 340, an optical sensor that detects when the plug 340 is within the receptacle 302, one or two sensors on the retention arms that detect when they are latched in place within the annular retention ring of the plug, etc. In one particular implementation, the connection detection sensor 1820 could be placed in a position such that when the plug is locked into place by the retention arms, the connection detection sensor 1820 indicates the plug is properly installed and seated, but when the plug is not within the receptacle, or is within the receptacle and not locked into place, the connection detection sensor 1820 indicates the plug is not properly installed and seated. In an alternative implementation, the connection detection sensor could detect a state of the retention arms to indicate whether the plug is present or not in the receptacle. In yet another alternative implementation, one sensor could detect the presence of the plug in the receptacle, and another sensor could detect the state of one or both of the retention arms. When the connection detection circuit 1810 receives an indication from the connection detection sensor 1820 that the plug is either not within the receptacle, or is not properly seated within the receptacle, the connection detection circuit can take a suitable action to indicate the lack of a connection, such as sounding an audible alarm, sending a message to a nurse's station, etc.

Figure 19:
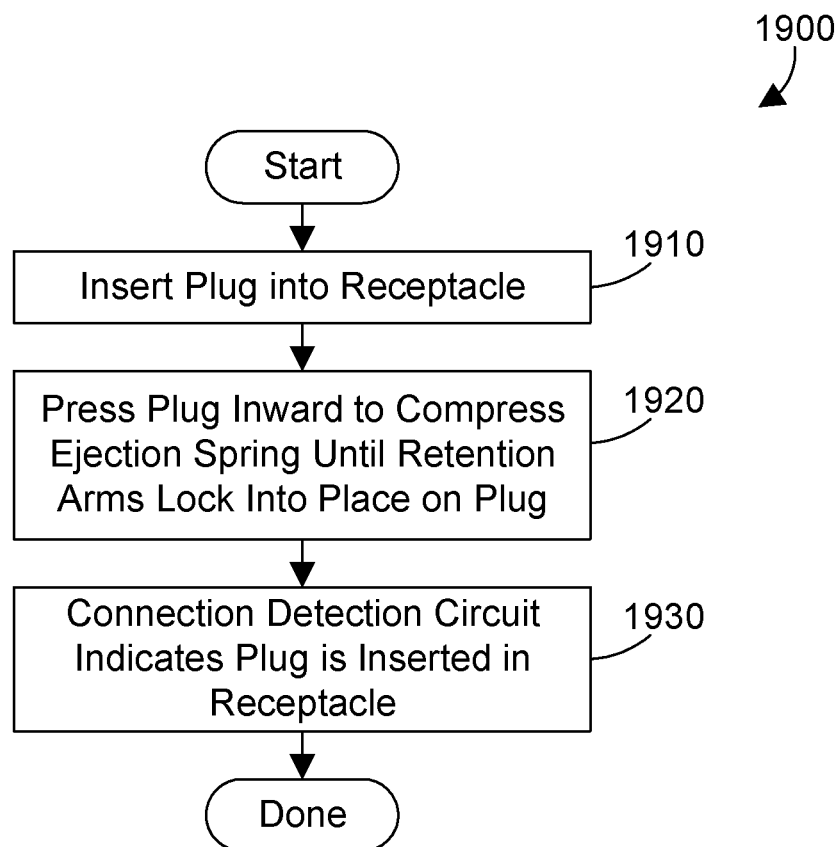
FIG. 19 is a flow diagram of one suitable method for mating the plug to the receptacle.

FIG. 19 shows a method 1900 for mating the plug to the receptacle. The plug is inserted into the receptacle (step 1910). At the beginning of step 1910, when the leading edge of the plug is placed in the opening of the receptacle, the leading edge of the plug contacts the beveled edges of the tip portions of the retention arms, causing the tip portions to separate enough for the body portion of the plug to continue sliding forward. This plug is slid forward until it contacts the ejection spring, and pressure is applied to compress the ejection spring until the retention arms lock into place on the plug (step 1920). The connection detection circuit indicates the plug is inserted in the receptacle (step 1930). Depending on the specific configuration, as discussed in detail in the preceding paragraph, the connection detection circuit 1810 can indicate the plug is inserted in the receptacle when the plug first enters the receptacle, or can wait until the plug is properly seated with the retention arms engaged before indicating the plug is inserted in the receptacle.

Figure 20:
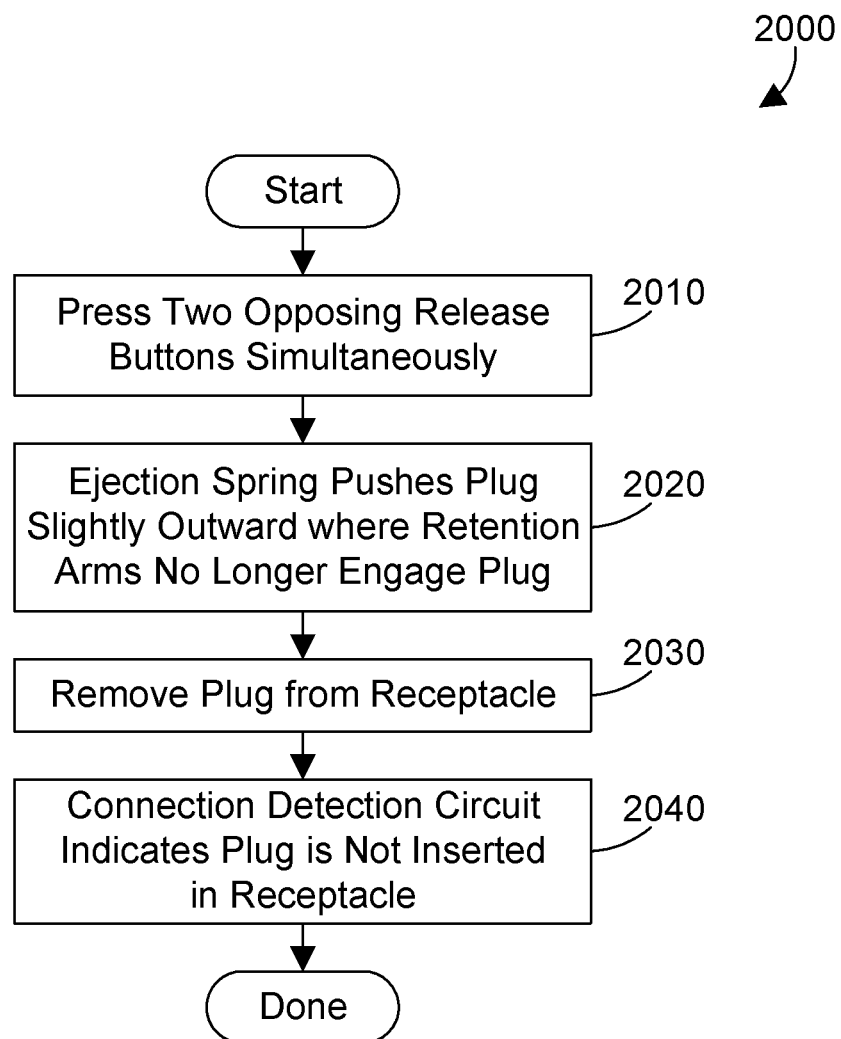
FIG. 20 is a flow diagram of one suitable method for unmating the plug from the receptacle.

Method 2000 in FIG. 20 shows how the plug is removed from the receptacle. The two opposing release buttons are pressed simultaneously (step 2010), which causes the tip portions of the retention arms to disengage from the annular recess of the plug. With the tip portions of the retention arms disengaged, the ejection spring pushes the plug slightly outward where the retention arms no longer engage the annular recess on the plug (step 2020). The plug is pulled until it is removed from the receptacle (step 2030). The connection detection circuit indicates the plug is not inserted in the receptacle (step 2040). As discussed above, the indication from the connection detection circuit can occur either when the retention arms are disengaged from the plug, or when the plug is completely removed from the receptacle.

Figure 21:
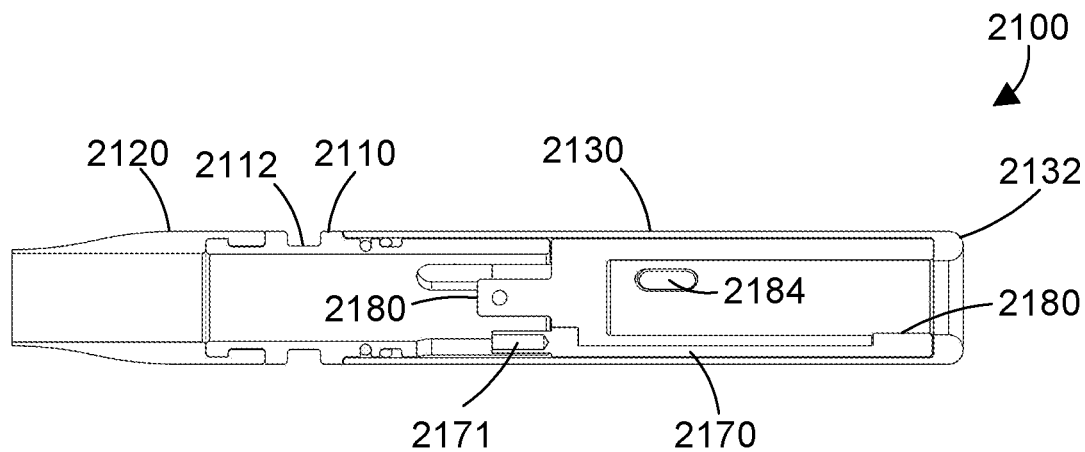
FIG. 21 is side cross-sectional view of a second implementation for a plug.
Figure 22:
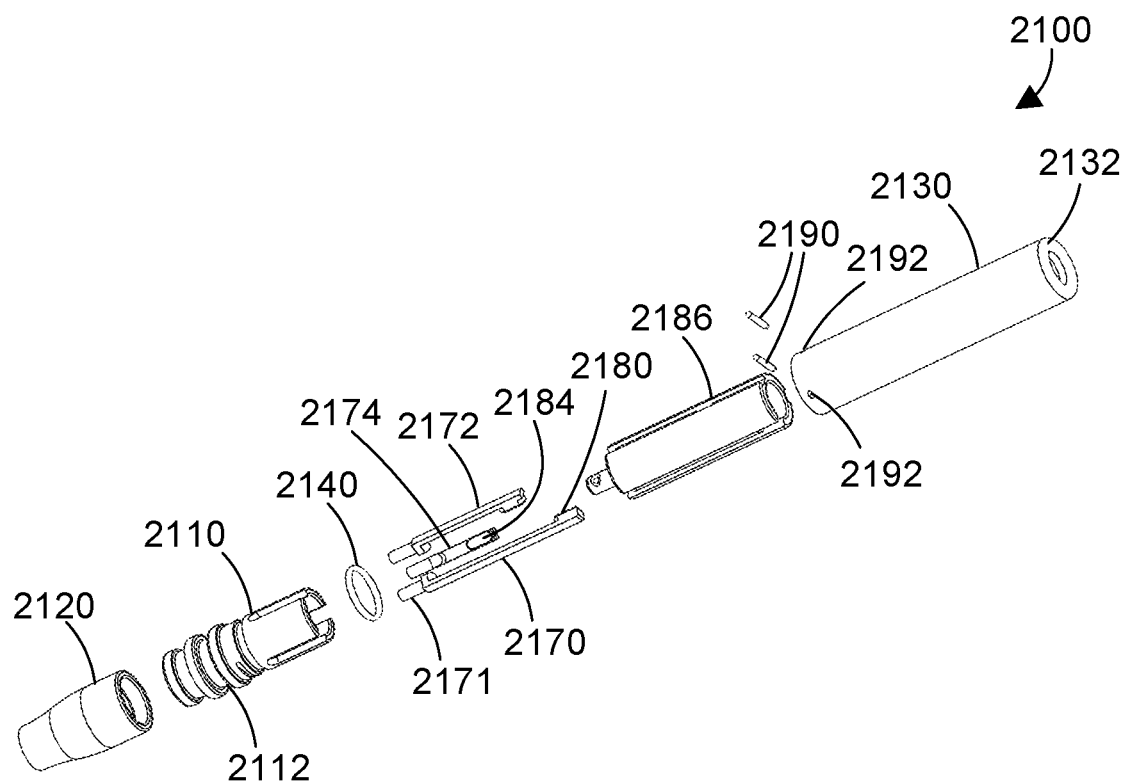
FIG. 22 is an exploded view of the plug in FIG. 21 showing its internal components.

Referring to FIGS. 21 and 22, an alternative implementation for a plug is shown as plug 2100. Plug 2100 includes a body portion 2110 coupled to a strain relief 2120. Electrical contacts 2170, 2172 and 2174 are housed within the body portion 2110 and a contact housing 2186. An outer sleeve 2130 captivates the internal components within the plug 2100. Once the electrical contacts 2170, 2172 and 2174 are placed within the body portion 2110 and the contact housing 2186, the outer sleeve 2130 is slid over the contact housing 2186, the electrical contacts 2170, 2172 and 2174 and over a portion of the body portion, and pins 2190 are then inserted through holes 2192 in the outer sleeve 2130 into corresponding holes in the body portion 2110 to captivate the internal plug components. The body portion 2110 includes an annular recess 2112 for receiving retaining arms to lock the plug within a receptacle. The outer sleeve 2130 includes a front edge 2132 that is preferably rounded or chamfered to allow the plug to push retaining arms out of the way while the plug is being pushed into a receptacle until the retaining arms in the receptacle lock into the annular recess 2112 to hold the plug in place.

The electrical contacts 2170, 2172 and 2174 preferably include a substantially linear contact, which is defined herein as a contact that has a length at least twice as long as its width. Each electrical contact 2170, 2172 and 2174 preferably includes a respective linear contact. In FIGS. 21 and 22, electrical contact 2170 is shown with a linear contact 2180, and electrical contact 2174 is show with a linear contact 2184. The linear contacts of the electrical contacts are the portion that make physical and electrical contact with corresponding contacts in the receptacle. The linear contact 2184 shown in FIG. 21 is an elongated oval in shape. This allows the contact to slide around an annular contact in a receptacle as a plug is rotated within the receptacle while maintaining good electrical contact. Each electrical contact includes a corresponding wire connection point. In FIGS. 21 and 22, electrical contact 2170 is shown to include a corresponding wire connection point 2171. A wire from a cable that passes through the strain relief 2120 into the interior of the connector 2100 may be attached to the wire connection point 2171 using any suitable connection, such as soldering, laser welding, crimping, etc. While not specifically identified with reference designators in FIG. 22 for the sake of clarity in the drawing, it is understood that electrical contacts 2172 and 2174 each include a corresponding wire connection point similar to wire connection point 2171 for electrical contact 2170 shown in FIG. 21.

Figure 23:
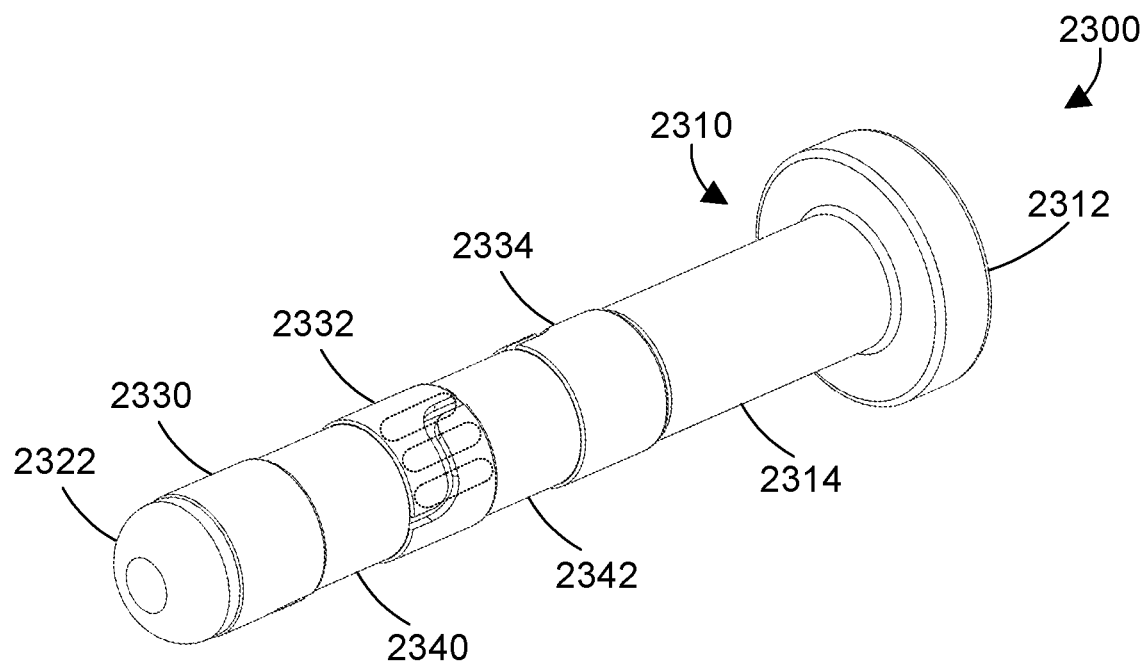
FIG. 23 is a perspective view of a second implementation for a contact assembly in a receptacle.
Figure 24:
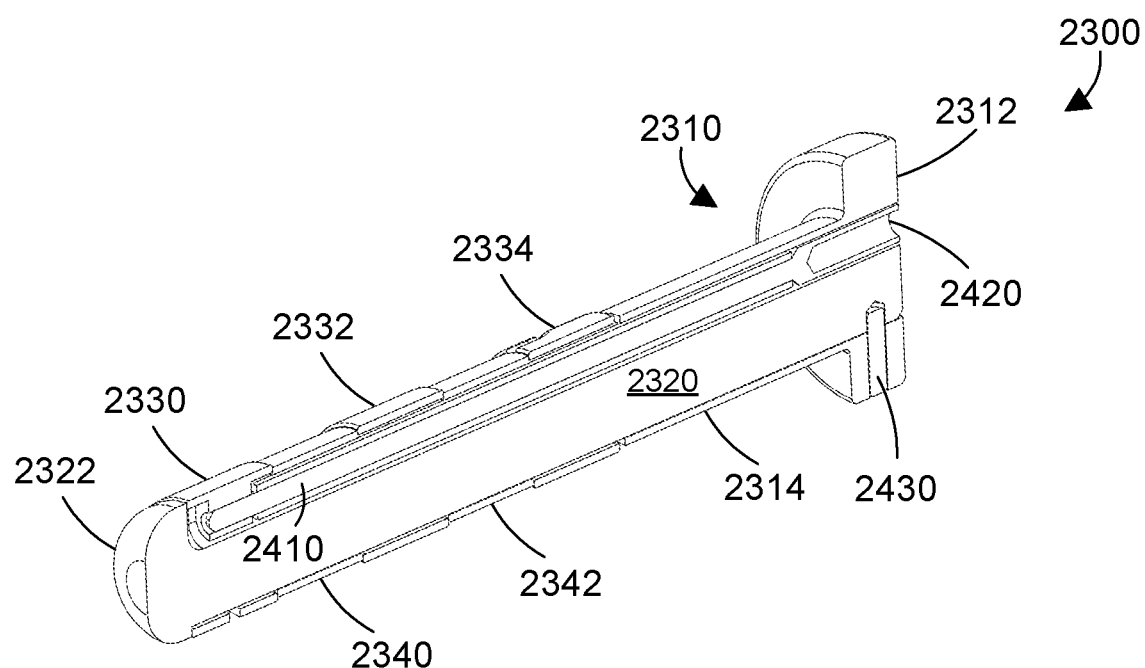
FIG. 24 is a perspective cross-sectional view of the contact assembly in FIG. 23.

The plug 2100 can be mated to a suitable contact assembly as shown in FIGS. 23 and 24. Contact assembly 2300 is a second implementation for the contact assembly within a receptacle. Contact assembly 2300 includes a base portion 2310 that includes a flange portion 2312 and a substantially cylindrical portion 2314 extending from the flange portion 2312. A core portion 2320 is attached to the base portion 2310 using a suitable fastener, such as a screw or a pin 2430 shown in FIG. 24. The core portion 2320 includes a rounded front portion 2322. The core portion 2320 supports three substantially annular electrical contacts 2330, 2332 and 2334, interposed by two insulator sleeves 2340 and 2342. Each electrical contact 2330, 2332 and 2334 are connected to respective connecting rods, which provide connection points to a wire in a cable. One advantage for the contact assembly 2300 shown in FIGS. 23 and 24 is that no printed circuit board is required. In FIG. 24, electrical contact 2330 is connected to a connecting rod 2410, which includes a wire connection point 2420 at the opposite end for connecting to a wire in a cable. The wire can be connected to the wire connection point 2420 in any suitable way, such as soldering, crimping, laser welding, etc. A careful review of the electrical contacts 2330, 2332 and 2334 in FIGS. 23 and 24 shows that in the preferred implementation they have a slightly larger diameter than the non-conductive portions 2322, 2340, 2342 and 2314. In addition, the electrical contacts 2330, 2332 and 2334 have rounded or chamfered edges, and an offset slit as shown on electrical contact 2332 in FIG. 23. The combination of the slightly larger diameter, the rounded or chamfered edges, and the offset slit give the electrical contacts 2330, 2332 and 2334 a spring-like action when a plug such as 2100 shown in FIGS. 21 and 22 is mated to the contact assembly 2300. The electrical contacts 2330, 2332 and 2334 are compressed to a slightly smaller diameter when mated with a plug and expand to their original diameter when the plug is removed. In this sense the electrical contacts 2330, 2332 and 2334 are spring-loaded contacts.

Figure 25:
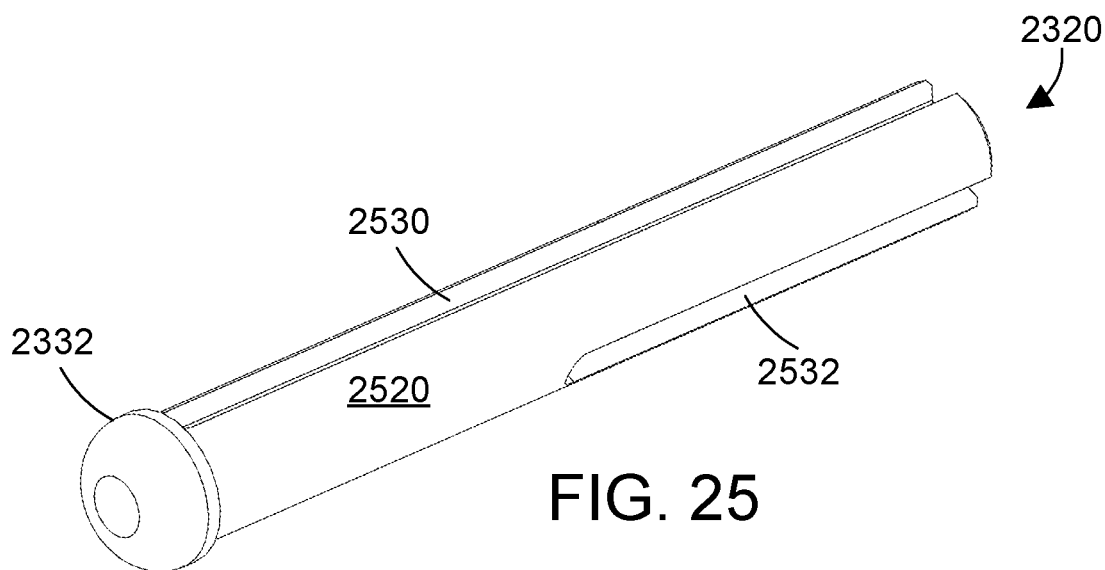
FIG. 25 is a perspective view of a core portion of the contact assembly in FIG. 23.

The core portion 2320 of the contact assembly 2300 shown in FIGS. 23 and 24 is shown in more detail in FIG. 25. The core portion 2320 includes a rounded front portion 2332 and an elongated center portion 2520 that includes slots for receiving the connecting rods and the interior portion of the electrical contacts. In the example shown in FIG. 25, the center portion 2520 includes a first slot 2530 that runs most of the length of the center portion 2520, and a second slot 2532 that runs only part of the length of the center portion 2520.

Figure 26:
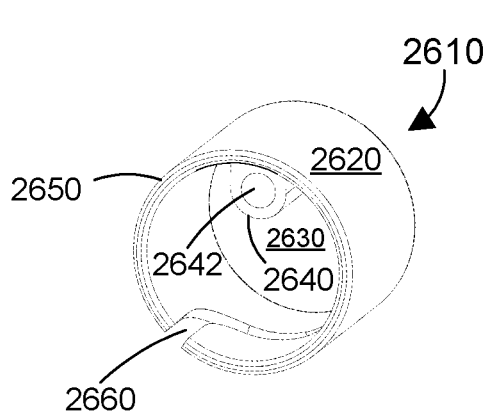
FIG. 26 is a perspective view of an annular contact ring used in the contact assembly in FIG. 23.
Figure 28:
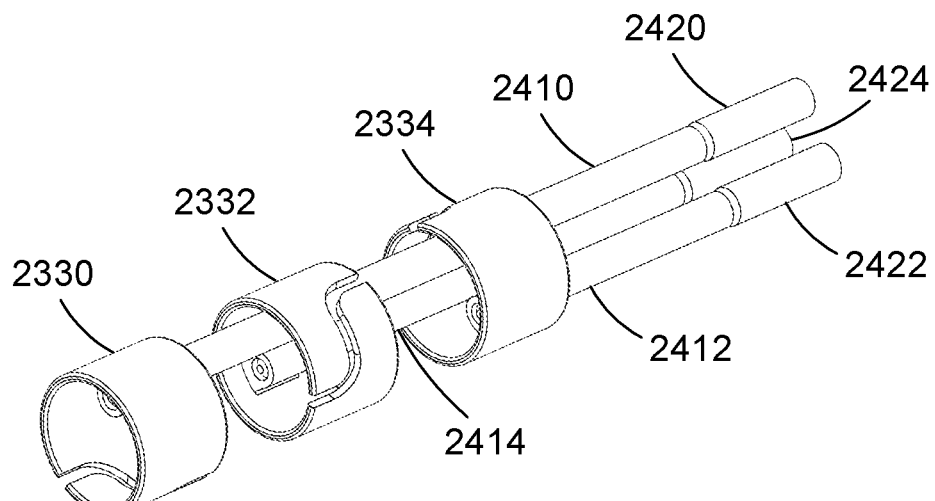
FIG. 28 is a perspective view showing how three annular contact rings are arranged in the contact assembly in FIG. 23.

One suitable implementation for the electrical contacts 2330, 2332 and 2334 shown in FIGS. 23 and 24 is shown at 2610 in FIG. 26. Electrical contact 2610 is an annular contact ring that includes a substantially cylindrical exterior portion 2620, a substantially hollow interior portion 2630, an interior connection point 2640 that includes a hollow interior 2642 for receiving a connecting rod, a rounded or chamfered edge 2650, and an offset slit 2660. This configuration allows the same electrical contact to be used for all three electrical contacts 2330, 2332 and 2334, as shown in FIGS. 23, 24 and 28, by offsetting each electrical contact 120 degrees from the other two electrical contacts as shown most clearly in FIG. 28. The slots in the center portion 2520 are dimensioned to receive the interior connection point of the electrical contacts and their respective connecting rods after the two have been connected in a suitable way, such as soldering, crimping or laser welding. Thus, slot 2530 shown in FIG. 25 receives the interior connection point 2640 of electrical contact 2330 with the attached connecting rod 2410 shown in FIG. 28. Similarly, the slot 2532 in FIG. 25 receives the interior connection point 2640 of electrical contact 2334 with its attached connecting rod 2412 shown in FIG. 28. The offset slit 2660 provides a slight gap that allows the annular contact ring 2610 to be slightly compressed in diameter when a plug is mated to a receptacle that includes the annular contact 2610. In addition, the offset slit 2660 provides a surface over which a linear contact, such as 2184 shown in FIG. 21, can slide around the annular contact without snagging or losing electrical connection. If the offset slit 2660 were replaced with a linear slit, the edge of a linear contact might grab the linear slit and prevent rotation of the plug within a receptacle. The offset slit provides a surface that assures the linear contact in a plug, which spans most or all of the width of the annular contact, will easily spin on the annular contact as the plug is rotated without snagging and while maintaining good electrical connection. This is illustrated graphically on the electrical contact 2332 in FIG. 23, where the phantom ovals represent the contact point for a linear contact similar to linear contact 2184 shown in FIG. 21. Because the slit in the electrical contact 2332 is offset, a linear contact in a plug that contacts the electrical contact 2332 will maintain good electrical connection without snagging as the plug is rotated, as illustrated by the three phantom ovals on electrical contact 2332 in FIG. 23.

Figure 27:
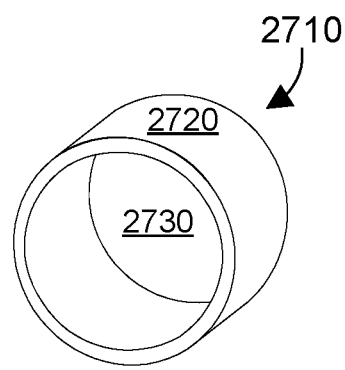
FIG. 27 is a perspective view of a cylindrical insulator sleeve used in the contact assembly in FIG. 23.

One suitable configuration for the insulator sleeves 2340 and 2342 shown in FIG. 23 are shown at 2710 in FIG. 27. Insulator sleeve 2710 is made of a material that is an electrical insulator, and has a substantially cylindrical configuration with an outer portion 2720 and a substantially hollow interior portion 2730. Conceptually, insulator sleeve 2710 resembles a section of plastic pipe.

The configuration shown in FIG. 28 makes it easy to see how these components are assembled with the core portion 2320. In the most preferred implementation, the three wires from a cable are connected to the wire connection points 2420, 2422 and 2424 of the three connection rods shown in FIG. 28, and the opposite ends of each connection rod is connected to a corresponding electrical contact. The first electrical contact 2330 with its attached connecting rod 2410 is slid into slot 2530. An insulator sleeve 2710 is then slid onto the center portion 2520, as shown at 2340 in FIG. 24. The second electrical contact 2332 with its attached connecting rod 2414 is slid into a corresponding slot that is not shown in FIG. 25 because the slot is on the back side of the center portion 2520. An insulator sleeve 2710 is then slid onto the center portion 2520, as shown at 2342 in FIG. 24. The third electrical contact 2334 with its attached connecting rod 2412 is slid into the corresponding slot 2532 shown in FIG. 25. At this point the cylindrical portion 2314 of the base portion 2310 is slid onto the center portion 2520, and the base portion 2310 is connected to the center portion 2520 of the core portion 2320 using a suitable fastener 2430, such as a pin or a screw, as shown in FIG. 24. Connecting the base portion 2310 to the core portion 2320 captivates the electrical contacts 2330, 2332 and 2334, and the insulator sleeves 2340 and 2342. The resulting assembled contact assembly 2300 is shown in cross-section in FIG. 29.

Figure 29:
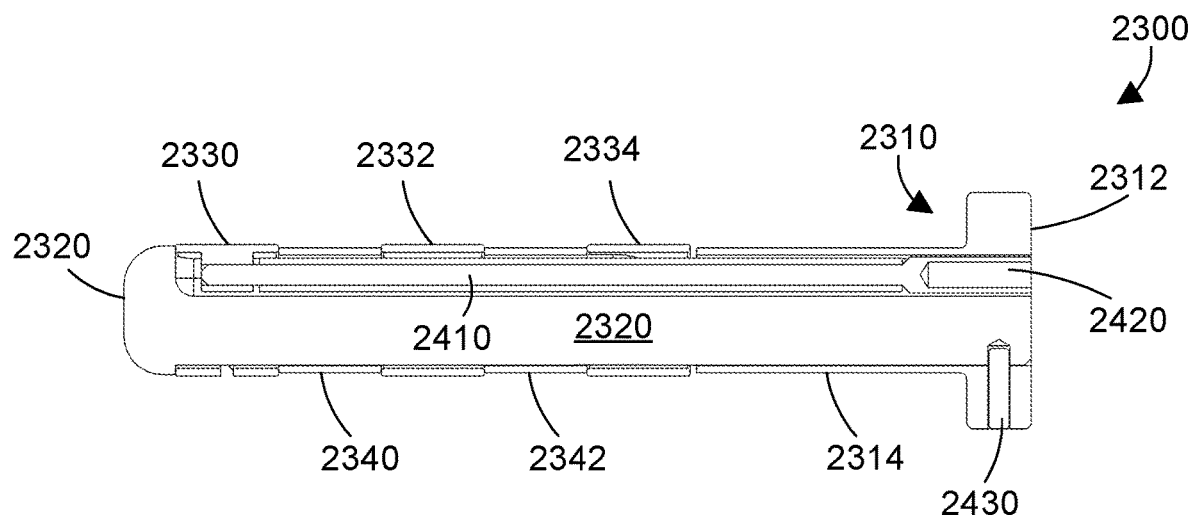
FIG. 29 is a side cross-sectional view of the contact assembly shown in FIGS. 23 and 24.

The contact assembly 2300 shown in FIGS. 23, 24 and 29 does not show a compression spring for the sake of clarity. However, it is within the scope of the disclosure and claims herein to include a compression spring similar to compression spring 1120 in FIGS. 11, 14 and 16 on the contact assembly 2300. Of course, any other suitable type or configuration of compression spring could also be used.

Figure 30:
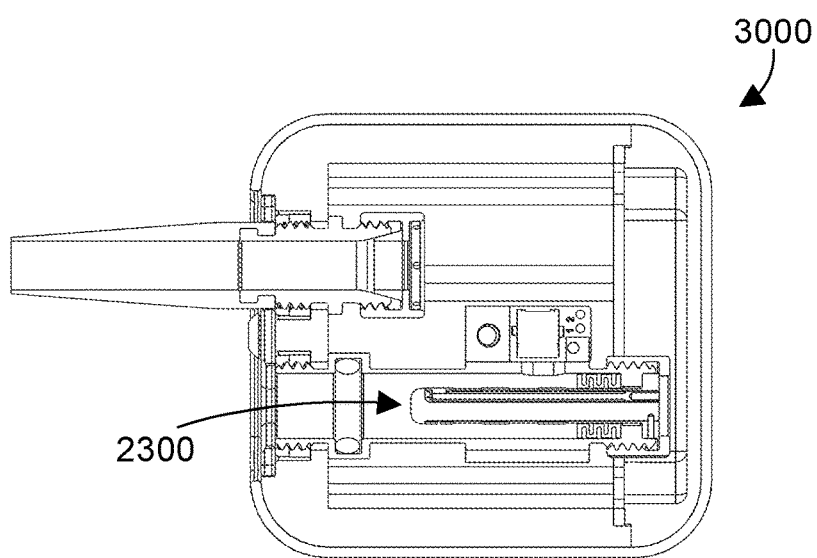
FIG. 30 is a side cross-sectional view of a second implementation for the receptacle that includes the contact assembly shown in FIGS. 23, 24 and 29.

FIG. 30 shows a receptacle 3000 that includes the contact assembly 2300 shown in FIGS. 23, 24 and 29. In one suitable implementation, the receptacle 3000 has the same configuration as receptacle 302 shown in FIGS. 3, 8, 9 and 10, with the exception that the contact assembly 840 has been replaced with the contact assembly 2300. Of course, receptacle 3000 could also have a configuration that is different than receptacle 302.

Figure 31:
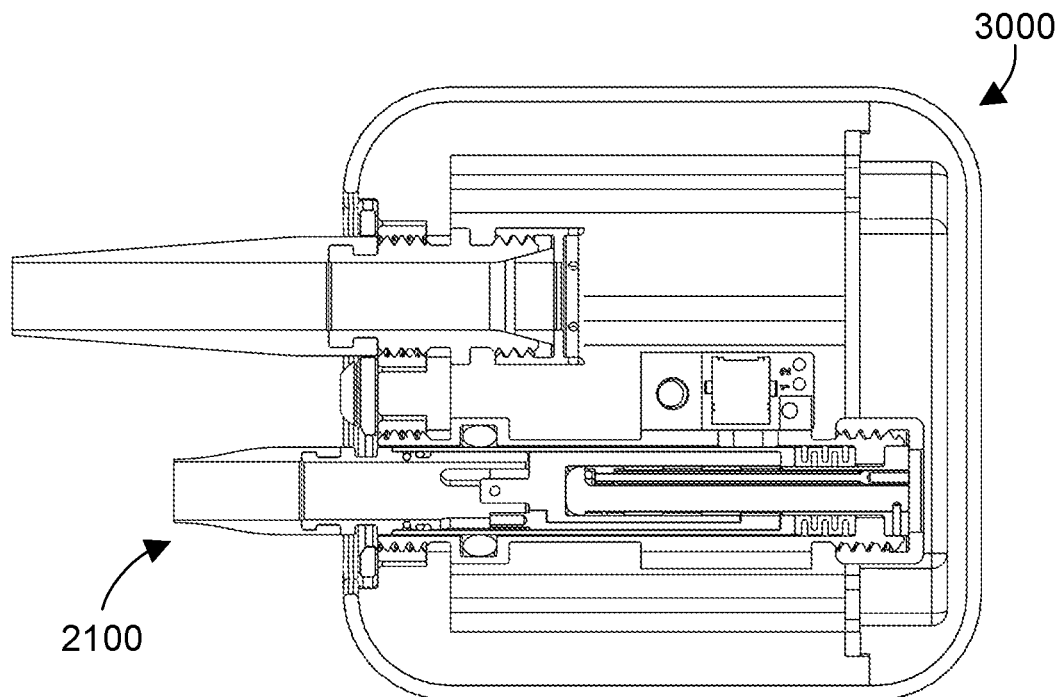
FIG. 31 is a side cross-sectional view of the receptacle in FIG. 30 with the plug in FIGS. 21 and 22 plugged into the receptacle.

FIG. 31 shows the receptacle 3000 that includes the contact assembly 2300 as shown in FIG. 30 with a plug such as plug 2100 in FIGS. 21 and 22 mated to the receptacle 3000. Once properly mated, the linear contact of each electrical contact 2170, 2172 and 2174 in the plug will be in contact with a corresponding annular contact in the receptacle. Thus, electrical contact 2170 in the plug 2100 in FIGS. 21 and 22 will be in physical contact with electrical contact 2334 on the contact assembly 2300 shown in FIGS. 23, 24 and 29. Electrical contact 2172 in the plug 2100 in FIGS. 21 and 22 will be in physical contact with electrical contact 2332 on the contact assembly 2300 shown in FIGS. 23, 24 and 29. Electrical contact 2174 in the plug 2100 in FIGS. 21 and 22 will be in physical contact with electrical contact 2330 on the contact assembly 2300 shown in FIGS. 23, 24 and 29. Of these three connections, only the connection between the electrical contact 2170 in the plug 2100 and the annular contact ring electrical contact 2334 is shown, although the numerical reference designators are not included in FIG. 31 for the sake of clarity. The correspondence between electrical contacts in the plug and the annular contact ring electrical contacts can be best understood by the detailed description above with respect to the views in FIGS. 21-24 and 29.

Figure 32:
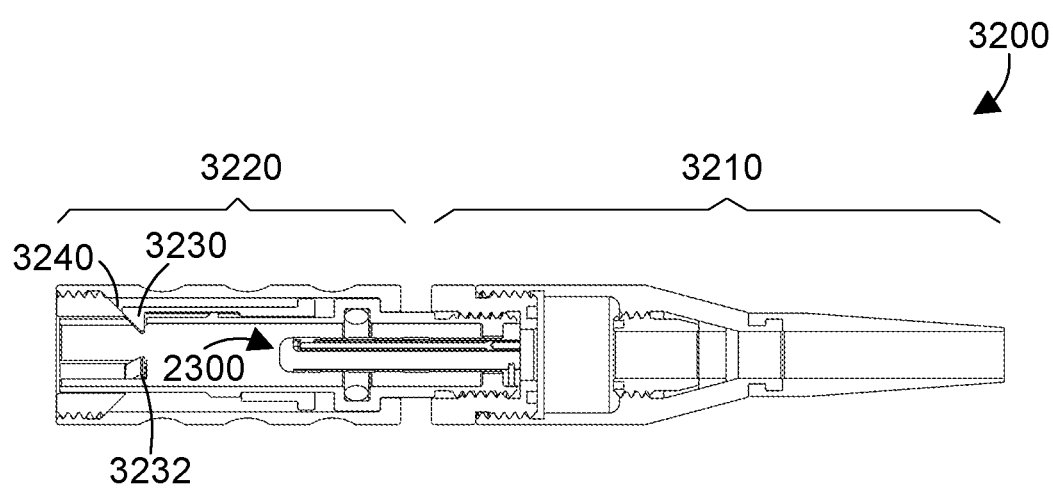
FIG. 32 is a side cross-sectional view of a third implementation for the receptacle that includes the contact assembly shown in FIGS. 23, 24 and 29.

Instead of having a box-like receptacle as shown in FIGS. 3, 8-10, 30 and 31, the receptacle could instead have a lower-profile inline design, as shown at receptacle 3200 in FIG. 32. In the specific configuration shown in FIG. 32, the receptacle 3200 includes a back portion 3210 and a front portion 3220. The front portion 3220 preferably slides towards the back portion 3210 against the bias of retaining arms 3230. As the front portion 3220 slides towards the back portion 3210, one or more ramp members 3240 push the retaining arms 3230 and 3232 to a retracted position where they no longer engage the annular recess 2112 on the plug 2100, thereby releasing the plug 2100 so it can be pulled and removed from the receptacle. When the pressure from sliding the front portion 3220 to the back portion 3210 is removed, the bias of the retaining arms 3230 and 3232 will cause the front portion 3220 to slide away from the back portion, back to the position shown in FIG. 32. The inline receptacle 3200 preferably includes the contact assembly 2300 discussed in detail above. In an alternative configuration, the inline receptacle 3200 could include the contact assembly 840 shown in FIGS. 8-11.

Figure 33:
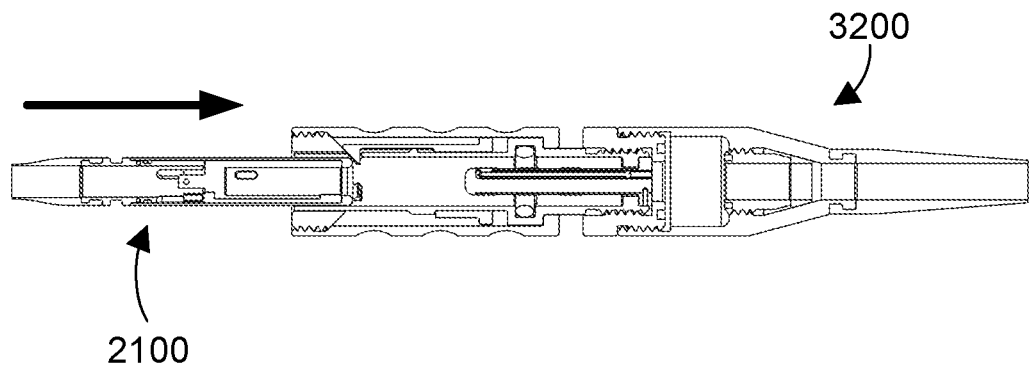
FIG. 33 is a side cross-sectional view of the receptacle in FIG. 32 with the plug in FIG. 21 being inserted into the receptacle.
Figure 34:
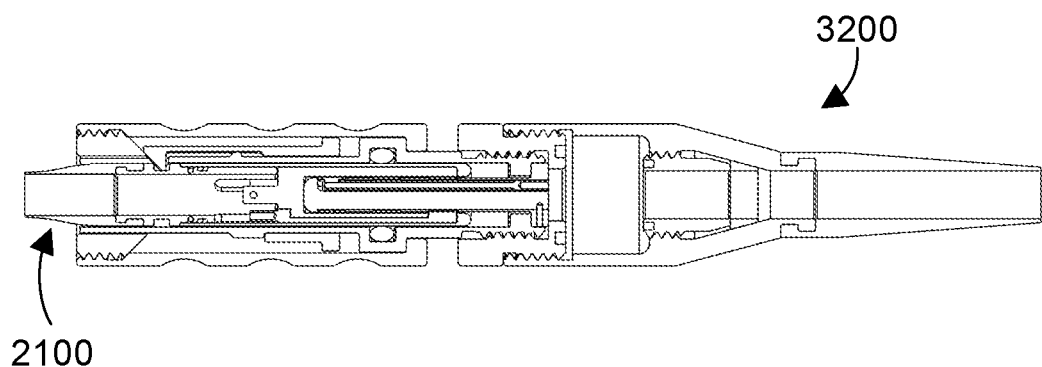
FIG. 34 is a side cross-sectional view of the receptacle in FIGS. 32 and 33 with the plug fully seated into the receptacle.

The mating of a plug 2100 to the receptacle 3200 is shown in FIG. 33. As discussed above, the plug 2100 includes a rounded or chamfered front surface so that when the plug encounters the retaining arms shown in FIGS. 32 and 33, continuing to push the plug into the receptacle as shown by the large arrow in FIG. 33 causes the plug to overcome the bias of the retaining arms so the plug can continue sliding into the receptacle 3200 onto the contact assembly. Because the annular contacts on the contact assembly are slightly larger in diameter than the internal diameter of the plug, pushing the plug onto the contact assembly causes the rounded or chamfered front edge of the plug to encounter the rounded edge of the first annular contact, which causes the annular contact to compress slightly in diameter. This compression is possible due to the offset slit 2660 shown in FIG. 26, which provides a small gap that provides the room needed for the annular contact to compress slightly as the plug is slid over the annular contact. This happens for all three annular contacts, one at a time, as the plug is slid onto the contact assembly. The result is the annular contacts in the contact assembly are slightly compressed by the plug assuring good electrical connection between the plug and the receptacle. When the contact assembly includes a compression spring, the compression spring is slightly compressed. Once the plug 2100 is fully seated into the receptacle 3200, as shown in FIG. 34, the retaining arms in the receptacle 3200 engage the annular recess in the plug 2100, thereby retaining the plug 2100 within the receptacle 3200.

Figure 35:
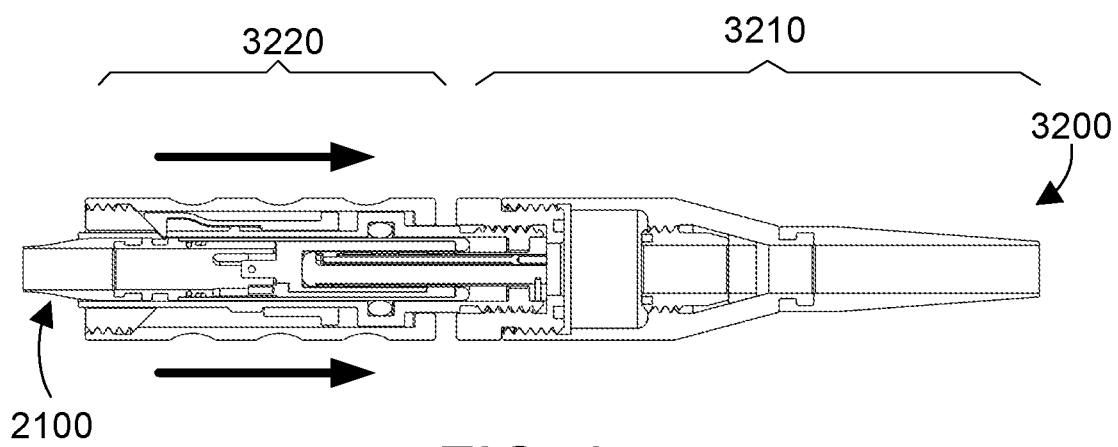
FIG. 35 is a side cross-sectional view of the plug and receptacle in FIG. 34 with a front portion of the receptacle slid towards the back section of the receptacle to disengage the retaining arms in the receptacle from the plug.

The plug 2100 can be removed from the receptacle 3200 as shown in FIG. 35. The front portion 3220 of the plug is pushed towards the back portion 3210 so the front portion 3220 slides with respect to the back portion 3210 in the direction of the large arrows shown in FIG. 35. Sliding the front portion 3220 towards the back portion 3210 causes the ramp member(s) to move the retaining arm(s) on the receptacle so they no longer engage the annular recess on the plug, as shown in FIG. 35. Once the retaining arm(s) no longer engage the annular recess on the plug, the plug may be removed from the receptacle.

Figure 36:
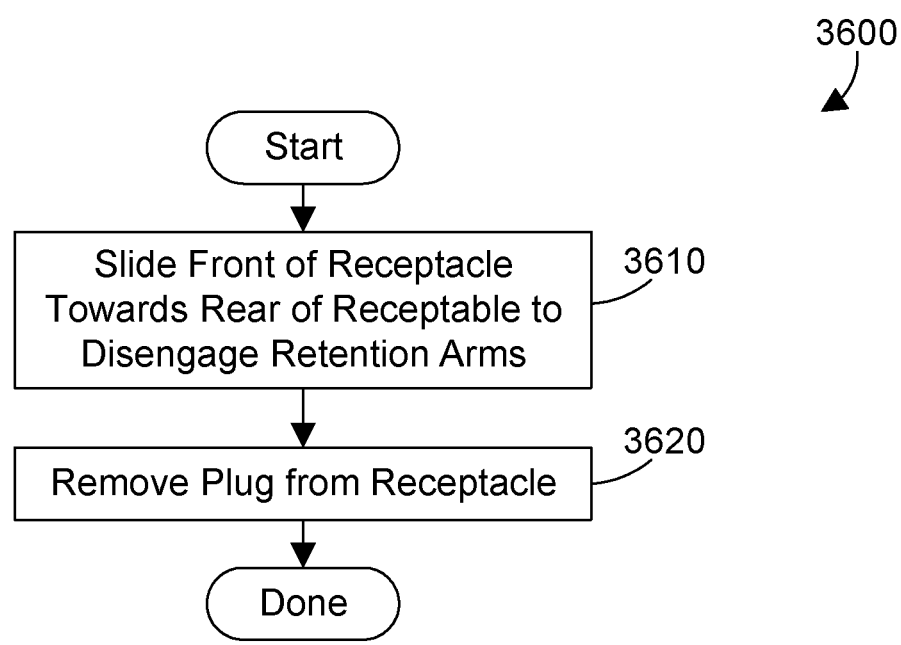
FIG. 36 is a flow diagram of a method for removing the plug in FIGS. 34 and 35 from the receptacle.

Referring to FIG. 36, a method 3600 shows how to remove the plug 2100 from the receptacle 3200 in FIG. 35. Slide the front of the receptacle towards the rear of the receptacle to disengage the retention arms (step 3610). Remove the plug from the receptacle (step 3620). Note the manner of removing the plug from the inline receptacle 3200 involves sliding the front portion of the receptacle towards the back portion to disengage the retention arms. This is a different release mechanism that the two opposed push buttons in the receptacle shown in FIGS. 3 and 8-10. When the receptacle includes an ejection spring, sliding the front of receptacle towards the rear of receptacle to disengage the retention arms will cause the ejection spring to move the plug slightly so the retention arms no longer engage the annular slot on the plug, allowing the plug to be removed from the receptacle in step 3620 without having to maintain the front portion in a slid position with respect to the back portion.

The plug and contact assembly can be made of any suitable materials. The preferred material is plastic. For example, these could be made from a polymer compound known as polyether ether ketone (PEEK). Of course, any suitable material that provides the required rigidity and electrical insulating characteristics could be used, whether currently known or developed in the future.

An electrical connector includes a plug that mates with a receptacle. In a medical application, the plug is connected to electrical leads that pass through a patient's skin to an implanted medical device in the patient's body. The receptacle is connected to external medical equipment. The plug is small in diameter, preferably not much larger in diameter than the cable to which the plug is attached, so the size of the opening in the skin can be minimized. All electrical contacts in the plug are on internal portions, minimizing any risk of electrical shock to the patient. The receptacle includes annular contacts that contact the internal electrical contacts on the plug when the plug and receptacle are properly mated. The receptacle preferably includes an ejection spring and one or more retention arms. When the plug is plugged into the receptacle, the plug is pushed to compress the ejection spring, which causes the spring-loaded retention arms to lock into place, retaining the plug in the receptacle. The receptacle may also include a connection detection sensor that detects when the plug is inserted, allowing external equipment connected to the receptacle to receive an indication regarding whether the plug is connected or not. This could allow, for example, the external equipment to notify a user when it detects the plug is removed from the receptacle.

The advantages of the connector disclosed and claimed herein include providing a plug outside the body that has internal electrical contacts that prevent accidental shock hazards in compliance with IEC 60601-1 Subclause 8.5.2.3. The diameter of the plug is only slightly larger than the diameter of the cable, thereby allowing passing the cable through a smaller incision in the patient's body when compared to prior art connectors, thereby reducing a potential infection site. For example, when a 0.138 inch (3.5 mm)

diameter cable is used, a prior art connector has a diameter of 0.43 inch (10.9 mm). The prior art connector is thus over three times the diameter of the cable. In one preferred implementation, when a 0.138 inch (3.5 mm) diameter cable is used, the plug disclosed herein has a preferred dimension of 0.180 inch (4.6 mm), which is only 30% larger than the cable itself. The smaller plug size reduces the size of the needed incision, which reduces the likelihood of infection at the site where the cable passes through the skin. The connection detection sensor detects when the plug is mated to the receptacle, allowing external equipment to sound an alarm or take other action when it detects the plug is not mated to the receptacle. The combination of the ejection spring and the retention arms create a positive lock so the plug is locked into place once properly seated within the receptacle. The annular contact points mean the plug does not have to be inserted into the receptacle at any particular orientation, which means the plug is omnidirectional with respect to the receptacle. In addition, the annular contact points allow rotating the plug while maintaining all electrical connections. The retention arms lock the plug into the receptacle until a person presses on two opposing release buttons simultaneously, or slides part of the receptacle to disengage the retention arms, which prevents accidentally disconnecting the plug from the receptacle. The result is a connector that is safe, reliable and easy to use.

What makes the connector omnidirectional, allowing the plug to be rotated freely within the receptacle while maintaining good electrical contact, is the presence of annular contacts in either the plug or the receptacle with corresponding electrical contacts on the other that contact the annular contacts. In a first implementation of the connector shown in FIGS. 3-17, the plug includes annular contacts while the receptacle includes contacts that contact the annular contacts in the plug when the plug is properly mated to the receptacle. In a second implementation of the connector shown in FIGS. 21-35, the receptacle includes annular contacts while the plug includes contacts that contact the annular contacts in the receptacle when the plug is properly mated to the receptacle. The disclosure and claims herein extend to any configuration that includes annular contacts on either the plug or the receptacle, with contacts in the other that make contact with those annular contacts.

While the connector has been discussed herein in the context of a medical connector that is used to connect an implanted medical device in a patient's body to external equipment, the connector is not limited to this medical environment. The structure and features disclosed and claimed herein could be used in any suitable connector in any suitable environment.

An electrical connector includes a plug that mates with a receptacle. In a medical application, the plug is connected to electrical leads that pass through a patient's skin to an implanted medical device in the patient's body, while the receptacle is connected to external medical equipment. All electrical contacts in the plug are on internal portions. The receptacle includes annular contacts that contact the internal electrical contacts on the plug when the plug and receptacle are properly mated. The receptacle includes a plurality of annular electrical contacts that have a first diameter and are separated by a plurality of annular insulators having a second diameter smaller than the first diameter.

The disclosure and claims herein support an electrical connector comprising: a plug comprising a body portion having a plurality of electrical contacts on an interior of the body portion; and a receptacle comprising a plurality of annular electrical contacts that contact the plurality of electrical contacts on the plug when the plug is mated to the receptacle, wherein the plug can be rotated within the receptacle while maintaining electrical contact between the plurality of annular electrical contacts on the receptacle and the plurality of electrical contacts on the plug, wherein the plurality of annular electrical contacts have a first diameter and are separated by a plurality of annular insulators having a second diameter smaller than the first diameter.

The disclosure and claims herein further support an electrical connector comprising: (A) a plug comprising a substantially hollow and substantially cylindrical body portion comprising: an interior portion having a plurality of electrical contacts; and an annular recess on an exterior of the body portion; (B) a receptacle comprising: a plurality of annular electrical contacts that contact the plurality of electrical contacts when the plug is mated to the receptacle, wherein the plug can be rotated within the receptacle while maintaining electrical contact between the plurality of annular electrical contacts on the receptacle and the plurality of electrical contacts on the plug, wherein the plurality of annular electrical contacts have a first diameter and are separated by a plurality of annular insulators having a second diameter smaller than the first diameter; and at least one retention arm that engages the annular recess on the plug when the plug is properly mated with the receptacle to maintain the plug properly mated with the receptacle.

The disclosure and claims herein additionally support an electrical connector comprising: (A) a plug comprising a substantially hollow and substantially cylindrical body portion comprising: an interior portion having a plurality of electrical contacts; and an annular recess on an exterior of the body portion; (B) a receptacle comprising: a plurality of annular electrical contacts that contact the plurality of electrical contacts when the plug is mated to the receptacle, wherein the plug can be rotated within the receptacle while maintaining electrical contact between the plurality of annular electrical contacts on the receptacle and the plurality of electrical contacts on the plug, wherein the plurality of annular electrical contacts have a first diameter and are separated by a plurality of annular insulators having a second diameter smaller than the first diameter; wherein each of the plurality of annular electrical contacts in the receptacle comprises: a substantially cylindrical exterior portion; a substantially hollow interior portion; and an interior connection point that includes a hollow interior for receiving a connecting rod; wherein each of the plurality of annular insulators in the receptacle comprises: a substantially cylindrical configuration with an outer portion and a substantially hollow interior portion that resembles a section of plastic pipe.

One skilled in the art will appreciate that many variations are possible within the scope of the claims. Thus, while the disclosure is particularly shown and described above, it will be understood by those skilled in the art that these and other changes in form and details may be made therein without departing from the spirit and scope of the claims.

The invention claimed is:

1. An electrical connector comprising:
a plug comprising a body portion having a plurality of electrical contacts on an interior of the body portion; and
a receptacle comprising a plurality of annular electrical contacts that contact the plurality of electrical contacts on the plug when the plug is mated to the receptacle, wherein the plug can be rotated within the receptacle while maintaining electrical contact between the plurality of annular electrical contacts on the receptacle and the plurality of electrical contacts on the plug, wherein the plurality of annular electrical contacts have a first diameter and are separated by a plurality of individual and separate annular insulators having a second diameter smaller than the first diameter.

2. The electrical connector of claim 1 wherein each of the plurality of annular electrical contacts in the receptacle comprises:
   a substantially cylindrical exterior portion;
   a substantially hollow interior portion; and
   an interior connection point that includes a hollow interior for receiving a connecting rod.

3. The electrical connector of claim 2 where each of the plurality of annular electrical contacts in the receptacle further comprises:
   a rounded or chamfered edge; and
   an offset slit.

4. The electrical connector of claim 1 wherein each of the plurality of annular insulators in the receptacle comprises:
   a substantially cylindrical configuration with an outer portion and a substantially hollow interior portion that resembles a section of plastic pipe.

5. The electrical connector of claim 1 wherein each of the plurality of annular electrical contacts in the receptacle comprises a substantially cylindrical member having an offset slit that gives each of the plurality of annular electrical contacts a spring-like action when the plug is mated to the receptacle.

6. The electrical connector of claim 5 wherein plugging the plug into the receptacle causes each of the plurality of annular electrical contacts to compress to a slightly smaller diameter, thereby providing the spring-like action that maintains contact with a corresponding electrical contact in the plug.

7. The electrical connector of claim 1 wherein the plug comprises an annular recess on an exterior of the body portion, and wherein the receptacle comprises at least one retention arm that engages the annular recess on the plug when the plug is properly mated with the receptacle to maintain the plug properly mated with the receptacle.

8. The electrical connector of claim 7 wherein the at least one retention arm comprises two retention arms pivotally coupled to a same pivot point to provide a scissor-like action with respect to each other, each retention arm comprising a tip portion configured to engage the annular recess on the plug, wherein the electrical connector further comprises a spring between the two retention arms to bias the tip portions in a closed position.

9. The electrical connector of claim 8 wherein each tip portion of the two retention arms comprises a beveled front surface that allows the plug to slide along the beveled front surface to partially separate the tip portions, the two tip portions of the two retention arms separating from each other and sliding along the body of the plug as the plug is pushed into the receptacle until the plug is in a desired position, at which point the two tip portions engage the annular recess in the plug to keep the plug mated to the receptacle.

10. The electrical connector of claim 8 wherein the receptacle comprises an ejection spring that is compressed by the plug for the tip portions of the retention arms to engage the annular recess in the plug.

11. The electrical connector of claim 7 wherein the receptacle further comprises a movable portion and a fixed portion, wherein the movable portion slides with respect to the fixed portion, wherein the movable portion on the receptacle disengages the at least one retention arm from the annular recess on the plug when the movable portion is slid with respect to the fixed portion of the receptacle.

12. An electrical connector comprising:
   (A) a plug comprising a substantially hollow and substantially cylindrical body portion comprising:
      an interior portion having a plurality of electrical contacts; and
      an annular recess on an exterior of the body portion;
   (B) a receptacle comprising:
      a plurality of annular electrical contacts that contact the plurality of electrical contacts when the plug is mated to the receptacle, wherein the plug can be rotated within the receptacle while maintaining electrical contact between the plurality of annular electrical contacts on the receptacle and the plurality of electrical contacts on the plug, wherein the plurality of annular electrical contacts have a first diameter and are separated by a plurality of individual and separate annular insulators having a second diameter smaller than the first diameter; and
      at least one retention arm that engages the annular recess on the plug when the plug is properly mated with the receptacle to maintain the plug properly mated with the receptacle.

13. The electrical connector of claim 12 wherein each of the plurality of annular electrical contacts in the receptacle comprises:
   a substantially cylindrical exterior portion;
   a substantially hollow interior portion; and
   an interior connection point that includes a hollow interior for receiving a connecting rod.

14. The electrical connector of claim 13 where each of the plurality of annular electrical contacts in the receptacle further comprises:
   a rounded or chamfered edge; and
   an offset slit.

15. The electrical connector of claim 12 wherein each of the plurality of annular insulators in the receptacle comprises:
   a substantially cylindrical configuration with an outer portion and a substantially hollow interior portion that resembles a section of plastic pipe.

16. The electrical connector of claim 12 wherein each of the plurality of annular electrical contacts in the receptacle comprises a substantially cylindrical member having an offset slit that gives each of the plurality of annular electrical contacts a spring-like action when the plug is mated to the receptacle.

17. The electrical connector of claim 12 wherein the at least one retention arm comprises two retention arms pivotally coupled to a same pivot point to provide a scissor-like action with respect to each other, each retention arm comprising a tip portion configured to engage the annular recess on the plug, wherein the electrical connector further comprises a spring between the two retention arms to bias the tip portions in a closed position, wherein each tip portion of the two retention arms comprises a beveled front surface that allows the plug to slide along the beveled front surface to partially separate the tip portions, the two tip portions of the two retention arms separating from each other and sliding along the body of the plug as the plug is pushed into the receptacle until the plug is in a desired position, at which point the two tip portions engage the annular recess in the plug to keep the plug mated to the receptacle.

18. The electrical connector of claim 17 wherein the receptacle further comprises an ejection spring that is compressed by the plug for the two tip portions of the retention arms to engage the annular recess in the plug.

19. The electrical connector of claim 17 wherein the receptacle further comprises a movable portion and a fixed portion, where the movable portion slides with respect to the fixed portion, wherein the movable portion disengages the two retention arms from the annular recess on the plug when the movable portion is slid with respect to the fixed portion of the receptacle.

20. An electrical connector comprising:
   (A) a plug comprising a substantially hollow and substantially cylindrical body portion comprising:
      an interior portion having a plurality of electrical contacts; and
      an annular recess on an exterior of the body portion;
   (B) a receptacle comprising:
      a plurality of annular electrical contacts that contact the plurality of electrical contacts when the plug is mated to the receptacle, wherein the plug can be rotated within the receptacle while maintaining electrical contact between the plurality of annular electrical contacts on the receptacle and the plurality of electrical contacts on the plug, wherein the plurality of annular electrical contacts have a first diameter and are separated by a plurality of annular insulators having a second diameter smaller than the first diameter;
   wherein each of the plurality of annular electrical contacts in the receptacle comprises:
      a substantially cylindrical exterior portion;
      a substantially hollow interior portion; and
      an interior connection point that includes a hollow interior for receiving a connecting rod;
   wherein each of the plurality of annular insulators in the receptacle comprises:
      a substantially cylindrical configuration with an outer portion and a substantially hollow interior portion that resembles a section of plastic pipe.

* * * * *